(12) United States Patent
Dunn-Coleman et al.

(10) Patent No.: US 9,102,929 B2
(45) Date of Patent: Aug. 11, 2015

(54) BGL6 BETA-GLUCOSIDASE AND NUCLEIC ACIDS ENCODING THE SAME

(71) Applicant: Danisco US Inc., Palo Alto, CA (US)

(72) Inventors: Nigel Dunn-Coleman, El Sauzal (ES); Michael Ward, San Francisco, CA (US)

(73) Assignee: Danisco US Inc., Palo Alto, CA (US)

(*) Notice: Subject to any disclaimer, the term of this patent is extended or adjusted under 35 U.S.C. 154(b) by 17 days.

(21) Appl. No.: 14/158,666

(22) Filed: Jan. 17, 2014

(65) Prior Publication Data

US 2014/0234931 A1 Aug. 21, 2014

Related U.S. Application Data

(60) Continuation of application No. 13/456,063, filed on Apr. 25, 2012, now Pat. No. 8,663,965, which is a division of application No. 12/506,745, filed on Jul. 21, 2009, now Pat. No. 8,278,079, which is a division of application No. 10/530,556, filed as application No. PCT/US03/35672 on Nov. 5, 2003, now Pat. No. 7,582,462.

(60) Provisional application No. 60/424,784, filed on Nov. 7, 2002.

(51) Int. Cl.
| | | |
|---|---|---|
| *A61K 38/47* | (2006.01) | |
| *C12P 7/06* | (2006.01) | |
| *C12N 9/42* | (2006.01) | |
| *A21D 8/04* | (2006.01) | |
| *C11D 3/386* | (2006.01) | |
| *C12P 7/14* | (2006.01) | |

(52) U.S. Cl.
CPC .............. *C12N 9/2437* (2013.01); *A21D 8/042* (2013.01); *C11D 3/38645* (2013.01); *C12N 9/244* (2013.01); *C12N 9/2445* (2013.01); *C12P 7/14* (2013.01); *C12Y 302/01021* (2013.01); *Y02E 50/17* (2013.01)

(58) Field of Classification Search
CPC .............. C12N 7/14; A61K 38/47; C12P 7/06
USPC .......... 435/161, 200, 252.3, 320.1; 424/94.61
See application file for complete search history.

(56) References Cited

U.S. PATENT DOCUMENTS 8,663,965 B2 * 3/2014 Dunn-Coleman et al. .... 435/200

* cited by examiner

*Primary Examiner* — Tekchand Saidha
(74) *Attorney, Agent, or Firm* — Danisco US Inc.

(57) ABSTRACT

The present invention provides a novel β-glucosidase nucleic acid sequence, designated bgl6, and the corresponding BGL6 amino acid sequence. The invention also provides expression vectors and host cells comprising a nucleic acid sequence encoding BGL6, recombinant BGL6 proteins and methods for producing the same.

15 Claims, 6 Drawing Sheets

FIGURE 1A    bgl6

```
GATCACACCC CTCCCACCCT TCTCTTTTCA AGGTTGTCCC CTTCTCCCAC    50
GGCTTTATGT ACTTCCCACT CTMTAATTCG CTCTTTCCAT TCCAAGCCAA    100
GCAACATCTG TGAGCAGCTC ATCCTTCCCA ATATGGGCGA ATGGCAGGAG    150
CAGATGATGG GTTTTGACGT GGAGGATGTT CTGTCTCAGC TGAGCCAAAA    200
TGAGAAGATT GCTCTCTTGT CCGGCATTGA TTTCTGGCAT ACTTATCCCA    250
TACCAAAGTA CAACGTCCCT TCAGTCCGCC TAACGGACGG TCCTAACGGC    300
ATACGAGGCA CAAAGTTTTT TGCTGGCATT CCTGCTGCCT GCCTGCCATG    350
TGGGACGGCC CTGGCCTCTA CCTGGGATAA GCAGCTGCTG AAGAAGGCTG    400
GGAAGCTGCT CGGTGATGAG TGCATCGCAA AAGGCGCCCA CTGCTGGCTG    450
GGCCCAACAA TCAATACTCC CCGATCTCCT CTGGGGGGGC GCGGCTTCGA    500
GTCATTTTCG GAAGATCCGT ACCTGTCCGG CATCCTTGCT GCATCTATGA    550
TTCTCGGCTG TGAAAGCACA GGTGTCATCT CTGCCGTCAA ACACTTTGTC    600
GCCAACGACC AGGAGCACGA GCGGCGAGCG GTCGACTGTC TCATCACCCA    650
GCGGGCTCTC CGGGAGGTCT ATCTGCGACC CTTCCAGATC GTAGCCCGAG    700
ATGCAAGGCC CGGCGCATTG ATGACATCCT ACAACAAGGT CAATGGCAAG    750
CACGTCGCTG ACAGCGCCGA GTTCCTTCAG GGCATTCTCC GGACTGAGTG    800
GAATTGGGAT CCTCTCATTG TCAGCGACTG GTACGGCACC TACACCACTA    850
TTGATGCCAT CAAAGCCGGC CTTGATCTCG AGATGCCGGG CGTTTCACGA    900
TATCGCGGCA AATACATCGA GTCTGCTCTG CAGGCCCGTT TGCTGAAGCA    950
GTCCACTATC GATGAGCGCG CTCGCCGCGT GCTCAGGTTC GCCCAGAAGG    1000
CCAGCCATCT CAAGGTCTCC GAGGTAGAGC AAGGCCGTGA CTTCCCAGAG    1050
GATCGCGTCC TCAACCGTCA GATCTGCGGC AGCAGCATTG TCCTACTGAA    1100
GAATGAGAAC TCCATCTTAC CTCTCCCCAA GTCCGTCAAG AAGGTCGCCC    1150
TTGTTGGATC CCACGTGCGT CTACCGGCTA TCTCGGGAGG AGGCAGCGCC    1200
TCTCTTGTCC CTTACTATGC CATATCTCTA TACGATGCCG TCTCTGAGGT    1250
ACTAGCCGGT GCCACGATCA CGCACGAGGT CGGTGCCTAT GCCCACCAAA    1300
TGCTGCCCGT CATCGACGCA ATGATCAGCA ACGCCGTAAT CCACTTCTAC    1350
AACGACCCCA TCGATGTCAA AGACAGAAAG CTCCTTGGCA GTGAGAACGT    1400
ATCGTCGACA TCGTTCCAGC TCATGGATTA CAACAACATC CCAACGCTCA    1450
ACAAGGCCAT GTTCTGGGGT ACTCTCGTGG GCGAGTTTAT CCCTACCGCC    1500
ACGGGAATTT GGAATTTGG CCTCAGTGTC TTTGGCACTG CCGACCTTTA    1550
TATTGATAAT GAGCTCGTGA TTGAAAATAC AACACATCAG ACGCGTGGTA    1600
CCGCCTTTTT CGGAAAGGGA ACGACGGAAA AAGTCGCTAC CAGGAGGATG    1650
GTGGCCGGCA GCACCTACAA GCTGCGTCTC GAGTTTGGGT CTGCCAACAC    1700
GACCAAGATG GAGACGACCG TGTTGTCAA CTTTGGCGGC GGTGCCGTAC    1750
ACCTGGGTGC CTGTCTCAAG GTCGACCCAC AGGAGATGAT TGCGCGGGCC    1800
GTCAAGGCCG CAGCCGATGC CGACTACACC ATCATCTGCA CGGGACTCAG    1850
CGGCGAGTGG GAGTCTGAGG GTTTTGACCG GCCTCACATG GACCTGCCCC    1900
CTGGTGTGGA CACCATGATC TCGCAAGTTC TTGACGCCGC TCCCAATGCT    1950
GTAGTCGTCA ACCAGTCAGG CACCCCAGTG ACAATGAGCT GGGCTCATAA    2000
```

FIGURE 1B    bgl6

| | | | | | |
|---|---|---|---|---|---|
| AGCAAAGGCC | ATTGTGCAGG | CTTGGTATGG | TGGTAACGAG | ACAGGCCACG | 2050 |
| GAATCTCCGA | TGTGCTCTTT | GGCAACGTCA | ACCCGTCGGG | GAAACTCTCC | 2100 |
| CTATCGTGGC | CAGTCGATGT | GAAGCACAAC | CCAGCATATC | TCAACTACGC | 2150 |
| CAGCGTTGGT | GGACGGGTCT | TGTATGGCGA | GGATGTTTAC | GTTGGCTACA | 2200 |
| AGTTCTACGA | CAAAACGGAG | AGGGAGGTTC | TGTTTCCTTT | TGGGCATGGC | 2250 |
| CTGTCTTACG | CTACCTTCAA | GCTCCCAGAT | TCTACCGTGA | GGACGGTCCC | 2300 |
| CGAAACCTTC | CACCCGGACC | AGCCCACAGT | AGCCATTGTC | AAGATCAAGA | 2350 |
| ACACGAGCAG | TGTCCCGGGC | GCCCAGGTCC | TGCAGCTATA | CATTTCGGCC | 2400 |
| CCAAACTCGC | CTACACATCG | CCCGGTCAAG | GAGCTGCACG | GATTCGAAAA | 2450 |
| GGTGTATCTT | GAAGCTGGCG | AGGAGAAGGA | GGTACAAATA | CCCATTGACC | 2500 |
| AGTACGCTAC | TAGCTTCTGG | GACGAGATTG | AGAGCATGTG | GAAGAGCGAG | 2550 |
| AGGGGCATTT | ATGATGTGCT | TGTAGGATTC | TCGAGTCAGG | AAATCTCGGG | 2600 |
| CAAGGGGAAG | CTGATTGTGC | CTGAAACGCG | ATTCTGGATG | GGGCTGTAGA | 2650 |
| TTCAACACGT | GAGCAAAAGC | GATTGCGGAA | AGTACCAGAA | AAGCCAAGGG | 2700 |
| AGTCAAAGGA | TGGGAACTTG | TGTCAATAGA | AGATATGCAT | GATGGGCATT | 2750 |
| TGGGATGGTG | TTTGGCATTA | TGCAAAGAAG | CAAAGATGGA | GTGATAAAAA | 2800 |
| AAAAAAAAAA | AA | | | | 2812 |

BGL6 amino acid sequence

```
MGEWQEQMMG FDVEDVLSQL SQNEKIALLS GIDFWHTYPI PKYNVPSVRL   50
TDGPNGIRGT KFFAGIPAAC LPCGTALAST WDKQLLKKAG KLLGDECIAK  100
GAHCWLGPTI NTPRSPLGGR GFESFSEDPY LSGILAASMI LGCESTGVIS  150
AVKHFVANDQ EHERRAVDCL ITQRALREVY LRPFQIVARD ARPGALMTSY  200
NKVNGKHVAD SAEFLQGILR TEWNWDPLIV SDWYGTYTTI DAIKAGLDLE  250
MPGVSRYRGK YIESALQARL LKQSTIDERA RRVLRFAQKA SHLKVSEVEQ  300
GRDFPEDRVL NRQICGSSIV LLKNENSILP LPKSVKKVAL VGSHVRLPAI  350
SGGGSASLVP YYAISLYDAV SEVLAGATIT HEVGAYAHQM LPVIDAMISN  400
AVIHFYNDPI DVKDRKLLGS ENVSSTSFQL MDYNNIPTLN KAMFWGTLVG  450
EFIPTATGIW EFGLSVFGTA DLYIDNELVI ENTTHQTRGT AFFGKGTTEK  500
VATRRMVAGS TYKLRLEFGS ANTTKMETTG VVNFGGGAVH LGACLKVDPQ  550
EMIARAVKAA ADADYTIICT GLSGEWESEG FDRPHMDLPP GVDTMISQVL  600
DAAPNAVVVN QSGTPVTMSW AHKAKAIVQA WYGGNETGHG ISDVLFGNVN  650
PSGKLSLSWP VDVKHNPAYL NYASVGGRVL YGEDVYVGYK FYDKTEREVL  700
FPFGHGLSYA TFKLPDSTVR TVPETFHPDQ PTVAIVKIKN TSSVPGAQVL  750
QLYISAPNSP THRPVKELHG FEKVYLEAGE EKEVQIPIDQ YATSFWDEIE  800
SMWKSERGIY DVLVGFSSQE ISGKGKLIVP ETRFWMGL             838
```

Figure 2

BGL6 amino acid sequence

```
MMGFDVEDVL  SQLSQNEKIA  LLSGIDFWHT  YPIPKYNVPS  VRLTDGPNGI   50
RGTKFFAGIP  AACLPCGTAL  ASTWDKQLLK  KAGKLLGDEC  IAKGAHCWLG  100
PTINTPRSPL  GGRGFESFSE  DPYLSGILAA  SMILGCESTG  VISAVKHFVA  150
NDQEHERRAV  DCLITQRALR  EVYLRPFQIV  ARDARPGALM  TSYNKVNGKH  200
VADSAEFLQG  ILRTEWNWDP  LIVSDWYGTY  TTIDAIKAGL  DLEMPGVSRY  250
RGKYIESALQ  ARLLKQSTID  ERARRVLRFA  QKASHLKVSE  VEQGRDFPED  300
RVLNRQICGS  SIVLLKNENS  ILPLPKSVKK  VALVGSHVRL  PAISGGGSAS  350
LVPYYAISLY  DAVSEVLAGA  TITHEVGAYA  HQMLPVIDAM  ISNAVIHFYN  400
DPIDVKDRKL  LGSENVSSTS  FQLMDYNNIP  TLNKAMFWGT  LVGEFIPTAT  450
GIWEFGLSVF  GTADLYIDNE  LVIENTTHQT  RGTAFFGKGT  TEKVATRRMV  500
AGSTYKLRLE  FGSANTTKME  TTGVVNFGGG  AVHLGACLKV  DPQEMIARAV  550
KAAADADYTI  ICTGLSGEWE  SEGFDRPHMD  LPPGVDTMIS  QVLDAAPNAV  600
VVNQSGTPVT  MSWAHKAKAI  VQAWYGGNET  GHGISDVLFG  NVNPSGKLSL  650
SWPVDVKHNP  AYLNYASVGG  RVLYGEDVYV  GYKFYDKTER  EVLFPFGHGL  700
SYATFKLPDS  TVRTVPETFH  PDQPTVAIVK  IKNTSSVPGA  QVLQLYISAP  750
NSPTHRPVKE  LHGFEKVYLE  AGEEKEVQIP  IDQYATSFWD  EIESMWKSER  800
GIYDVLVGFS  SQEISGKGKL  IVPETRFWMG  L                       831
```

Figure 3

```
ATGGGCGAAT GGCAGGAGCA GATGATGGGT TTTGACGTGG AGGATGTTCT    50
GTCTCAGCTG AGCCAAAATG AGAAGATTGC TCTCTTGTCC GGCATTGATT   100
TCTGGCATAC TTATCCCATA CCAAAGTACA ACGTCCCTTC AGTCCGCCTA   150
ACGGACGGTC CTAACGGCAT ACGAGGCACA AAGTTTTTG CTGGCATTCC    200
TGCTGCCTGC CTGCCATGTG GGACGGCCCT GGCCTCTACC TGGGATAAGC   250
AGCTGCTGAA GAAGGCTGGG AAGCTGCTCG GTGATGAGTG CATCGCAAAA   300
GGCGCCCACT GCTGGCTGGG CCCAACAATC AATACTCCCC GATCTCCTCT   350
GGGGGGGCGC GGCTTCGAGT CATTTTCGGA AGATCCGTAC CTGTCCGGCA   400
TCCTTGCTGC ATCTATGATT CTCGGCTGTG AAAGCACAGG TGTCATCTCT   450
GCCGTCAAAC ACTTTGTCGC CAACGACCAG GAGCACGAGC GGCGAGCGGT   500
CGACTGTCTC ATCACCCAGC GGGCTCTCCG GGAGGTCTAT CTGCGACCCT   550
TCCAGATCGT AGCCCGAGAT GCAAGGCCCG GCGCATTGAT GACATCCTAC   600
AACAAGGTCA ATGGCAAGCA CGTCGCTGAC AGCGCCGAGT TCCTTCAGGG   650
CATTCTCCGG ACTGAGTGGA ATTGGGATCC TCTCATTGTC AGCGACTGGT   700
ACGGCACCTA CACCACTATT GATGCCATCA AAGCCGGCCT TGATCTCGAG   750
ATGCCGGGCG TTTCACGATA TCGCGGCAAA TACATCGAGT CTGCTCTGCA   800
GGCCCGTTTG CTGAAGCAGT CCACTATCGA TGAGCGCGCT CGCCGCGTGC   850
TCAGGTTCGC CCAGAAGGCC AGCCATCTCA AGGTCTCCGA GGTAGAGCAA   900
GGCCGTGACT TCCCAGAGGA TCGCGTCCTC AACCGTCAGA TCTGCGGCAG   950
CAGCATTGTC CTACTGAAGA ATGAGAACTC CATCTTACCT CTCCCCAAGT  1000
CCGTCAAGAA GGTCGCCCTT GTTGGATCCC ACGTGCGTCT ACCGGCTATC  1050
TCGGGAGGAG GCAGCGCCTC TCTTGTCCCT TACTATGCCA TATCTCTATA  1100
CGATGCCGTC TCTGAGGTAC TAGCCGGTGC CACGATCACG CACGAGGTCG  1150
GTGCCTATGC CCACCAAATG CTGCCCGTCA TCGACGCAAT GATCAGCAAC  1200
GCCGTAATCC ACTTCTACAA CGACCCCATC GATGTCAAAG ACAGAAAGCT  1250
CCTTGGCAGT GAGAACGTAT CGTCGACATC GTTCCAGCTC ATGGATTACA  1300
ACAACATCCC AACGCTCAAC AAGGCCATGT TCTGGGGTAC TCTCGTGGGC  1350
GAGTTTATCC CTACCGCCAC GGGAATTTGG GAATTTGGCC TCAGTGTCTT  1400
TGGCACTGCC GACCTTTATA TTGATAATGA GCTCGTGATT GAAAATACAA  1450
CACATCAGAC GCGTGGTACC GCCTTTTTCG GAAAGGGAAC GACGGAAAAA  1500
GTCGCTACCA GGAGGATGGT GGCCGGCAGC ACCTACAAGC TGCGTCTCGA  1550
GTTTGGGTCT GCCAACACGA CCAAGATGGA GACGACCGGT GTTGTCAACT  1600
TTGGCGGCGG TGCCGTACAC CTGGGTGCCT GTCTCAAGGT CGACCCACAG  1650
GAGATGATTG CGCGGGCCGT CAAGGCCGCA GCCGATGCCG ACTACACCAT  1700
CATCTGCACG GGACTCAGCG GCGAGTGGGA GTCTGAGGGT TTTGACCGGC  1750
CTCACATGGA CCTGCCCCCT GGTGTGGACA CCATGATCTC GCAAGTTCTT  1800
GACGCCGCTC CCAATGCTGT AGTCGTCAAC CAGTCAGGCA CCCCAGTGAC  1850
AATGAGCTGG GCTCATAAAG CAAAGGCCAT TGTGCAGGCT TGGTATGGTG  1900
GTAACGAGAC AGGCCACGGA ATCTCCGATG TGCTCTTTGG CAACGTCAAC  1950
CCGTCGGGGA AACTCTCCCT ATCGTGGCCA GTCGATGTGA AGCACAACCC  2000
AGCATATCTC AACTACGCCA GCGTTGGTGG ACGGGTCTTG TATGGCGAGG  2050
ATGTTTACGT TGGCTACAAG TTCTACGACA AAACGGAGAG GGAGGTTCTG  2100
TTTCCTTTTG GGCATGGCCT GTCTTACGCT ACCTTCAAGC TCCCAGATTC  2150
TACCGTGAGG ACGGTCCCCG AAACCTTCCA CCCGGACCAG CCCACAGTAG  2200
CCATTGTCAA GATCAAGAAC ACGAGCAGTG TCCCGGGCGC CCAGGTCCTG  2250
```

FIGURE 4A

```
CAGCTATACA TTTCGGCCCC AAACTCGCCT ACACATCGCC CGGTCAAGGA        2300
GCTGCACGGA TTCGAAAAGG TGTATCTTGA AGCTGGCGAG GAGAAGGAGG        2350
TACAAATACC CATTGACCAG TACGCTACTA GCTTCTGGGA CGAGATTGAG        2400
AGCATGTGGA AGAGCGAGAG GGGCATTTAT GATGTGCTTG TAGGATTCTC        2450
GAGTCAGGAA ATCTCGGGCA AGGGGAAGCT GATTGTGCCT GAAACGCGAT        2500
TCTGGATGGG GCTGTAG                                           2517
```

Figure 4B

BGL6 BETA-GLUCOSIDASE AND NUCLEIC ACIDS ENCODING THE SAME

CROSS REFERENCE TO RELATED APPLICATIONS

This application is a continuation of U.S. patent application Ser. No. 13/456,063, now U.S. Pat. No. 8,663,965, which is a divisional of U.S. patent application Ser. No. 12/506,745, filed Jul. 21, 2009, now U.S. Pat. No. 8,278,079, which is a divisional of U.S. patent application Ser. No. 10/530,556, filed Oct. 11, 2005, now U.S. Pat. No. 7,582,462, which is a U.S. National Stage Application of International Application No. PCT/US03/35672, filed Nov. 5, 2003, which claims the benefit of U.S. Provisional Application No. 60/424,784, filed Nov. 7, 2002.

GOVERNMENT SUPPORT

Portions of this work were funded by Subcontract No. ZCO-30017-01 with the National Renewable Energy Laboratory under Prime Contract No. DE-AC36-99GO10337 with the U.S. Department of Energy. Accordingly, the United States Government may have certain rights in this invention.

SEQUENCE LISTING

The sequence listing submitted via EFS, in compliance with 37 C.F.R. §1.52(e), is incorporated herein by reference. The sequence listing text file submitted via EFS contains the file "30781-US-2-D2-C1-SEQLIST.txt", created on Apr. 30, 2014, which is 20,161 bytes in size.

FIELD OF THE INVENTION

The present invention relates to isolated bgl6 nucleic acid sequences which encode polypeptides having beta-glucosidase activity. The invention also relates to nucleic acid constructs, vectors, and host cells comprising the nucleic acid sequences as well as methods for producing recombinant BGL6 polypeptides.

REFERENCES

Altschul, S. F., et al., J. Mol. Biol. 215:403-410, 1990.
Altschul, S. F., et al., Nucleic Acids Res. 25:3389-3402, 1997.
Aro, N., et al., J. Biol. Chem., 10.1074/M003624200, Apr. 13, 2001.
Aubert, et al., Ed., p 11 et seq., Academic Press, 1988.
Ausubel G. M., et al. CURRENT PROTOCOLS IN MOLECULAR BIOLOGY, John Wiley & Sons, New York, N.Y., 1993.
Baldwin, D., et al., Curr. Opin. Plant Biol. 2(2):96-103, 1999.
Baulcombe, D., Arch. Virol. Suppl. 15:189-201, 1999.
Bhikhabhai, R. et al., J. Appl. Biochem. 6:336, 1984.
Brumbauer, A. et al., Bioseparation 7:287-295, 1999.
Carter et al., Nucl. Acids Res. 13:4331, 1986.
Chen et al., Biochem. Biophys. Acta. 1121:54-60, 1992.
Coligan, J. E. et al., eds., CURRENT PROTOCOLS IN IMMUNOLOGY, 1991.
Collen, A., et al., Journal of Chromatography A 910:275-284, 2001.
Coughlan, et al., BIOCHEMISTRY AND GENETICS OF CELLULOSE DEGRADATION.
Cummings and Fowler, Curr. Genet. 29:227-233, 1996.
Dayhoff et al. in Atlas of Protein Sequence and Structure, Volume 5, Supplement 3, Chapter 22, pp. 345-352, 1978.
Deutscher, M. P., Methods Enzymol. 182:779-80, 1990.
Doolittle, R. F., OF URFS AND ORFS, University Science Books, CA, 1986.
Ellouz, S. et al., J. Chromatography 396:307, 1987.
Fields and Song, Nature 340:245-246, 1989.
Filho, et al. Can. J. Microbiol. 42:1-5, 1996.
Fliess, A., et al., Eur. J. Appl. Microbiol. Biotechnol. 17:314, 1983.
Freer, et al. J. Biol. Chem. 268:9337-9342, 1993.
Freshney, R. I., ed., ANIMAL CELL CULTURE, 1987.
Goyal, A. et al. Bioresource Technol. 36:37, 1991.
Halldorsdottir, S et al., Appl Microbiol Biotechnol. 49(3): 277-84, 1998.
Hu et al., Mol Cell Biol. 11:5792-9, 1991.
Hemmpel, W. H. ITB Dyeing/Printing/Finishing 3:5-14, 1991.
Herr et al., Appl. Microbiol. Biotechnol. 5:29-36, 1978.
Jakobovits, A, et al., Ann N.Y. Acad Sci 764:525-35, 1995.
Jakobovits, A, Curr Opin Biotechnol 6(5):561-6, 1995.
Jones et al., Nature 321:522-525, 1986.
Kawaguchi, T et al., Gene 173(2):287-8, 1996.
Knowles, J. et al., TIBTECH 5, 255-261, 1987.
Kohler and Milstein, Nature 256:495, 1975.
Krishna, S. et al., Bioresource Tech. 77:193-196, 2001.
Kumar, A., et al., Textile Chemist and Colorist 29:37-42, 1997.
Lehtio, J. et al., FEMS Microbiology Letters 195:197-204, 2001.
Li and Ljungdahl Appl. Environ. Microbiol. 62:209-213, 1996.
Linder, M. and Teeri, T. T., Biotechnol. 57:15-28, 1997.
Medve, J. et al., J. Chromatography A 808:153, 1998.
Ohmiya et al., Biotechnol. Gen. Engineer. Rev. 14:365-414, 1997.
Ooi et al., Nucleic Acids Res. 18(19):5884, 1990.
Ortega et al., International Biodeterioration and Biodegradation 47:7-14, 2001.
Penttila et al., Yeast 3:175-185, 1987.
Penttila et al., Gene 63: 103-112, 1988.
Pere, J., et al., In Proc. Tappi Pulping Conf., Nashville, Tenn., 27-31, pp. 693-696, 1996.
Riechmann et al., Nature 332:323-327, 1988.
Rothstein et al., Gene 55:353-356, 1987.
Saarilahti et al., Gene 90:9-14, 1990.
Sakamoto et al., Curr. Genet. 27:435-439, 1995.
Saloheimo M, et al., Gene 63:11-22, 1988.
Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Spilliaert R, et al., Eur J Biochem. 224(3):923-30, 1994.
Stahlberg, J. et al., Bio/Technol. 9:286-290, 1991.
Strathern et al., eds. (1981) The Molecular Biology of the Yeast Saccharomyces.
Suurnakki, A. et al., Cellulose 7:189-209, 2000.
Te'o, J. et al., FEMS Microbiology Letters 190:13-19, 2000.
Tilbeurgh, H. et al., FEBS Lett. 16:215, 1984.
Timberlake et al., Cell 1:29-37, 1981.
Tomaz, C. and Queiroz, J., J. Chromatography A 865:123-128, 1999.
Tomme, P. et al., Eur. J. Biochem. 170:575-581, 1988.
Tormo, J. et al., EMBO J. 15:5739-5751, 1996.
Tyndall, R. M., Textile Chemist and Colorist 24:23-26, 1992.
Van Rensburg et al., Yeast 14:67-76, 1998.
Van Tilbeurgh, H. et al., FEBS Lett. 204:223-227, 1986.
Verhoeyen et al., Science 239:1534-1536, 1988.

Warrington, et al., *Genomics* 13:803-808, 1992.
Wells et al., Gene 34:315, 1985.
Wells et al., Philos. Trans. R. Soc. London SerA 317:415, 1986.
Wood, Biochem. Soc. Trans., 13, pp. 407-410, 1985.
Wood et al., METHODS IN ENZYMOLOGY, 160, 25, p. 87 et seq., Academic Press, New York, 1988.
Zoller et al., Nucl. Acids Res. 10:6487, 1987.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases ([beta]-D-glucoside glucohydrolase; EC 3.2.1.21) ("BG"). (Knowles et al., 1987; Shulein, 1988). Endoglucanases act mainly on the amorphous parts of the cellulose fibre, whereas cellobiohydrolases are also able to degrade crystalline cellulose (Nevalainen and Penttila, 1995). Thus, the presence of a cellobiohydrolase in a cellulase system is required for efficient solubilization of crystalline cellulose (Suurnakki, et al. 2000). Beta-glucosidase acts to liberate D-glucose units from cellobiose, cellooligosaccharides, and other glucosides (Freer, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. See, e.g., Aro et al., 2001; Aubert et al., 1988; Wood et al., 1988, and Coughlan, et al.

The fungal cellulase classifications of CBH, EG and BG can be further expanded to include multiple components within each classification. For example, multiple CBHs, EGs and BGs have been isolated from a variety of fungal sources including *Trichoderma reesei* which contains known genes for 2 CBHs, i.e., CBH I and CBH II, at least 5 EGs, EG I, EG II, EG III, EGIV and EGV, and at least 2 BGs, i.e., BG1 and BG2.

In order to efficiently convert crystalline cellulose to glucose the complete cellulase system comprising components from each of the CBH, EG and BG classifications is required, with isolated components less effective in hydrolyzing crystalline cellulose (Filho et al., 1996). A synergistic relationship has been observed between cellulase components from different classifications. In particular, the EG-type cellulases and CBH-type cellulases synergistically interact to more efficiently degrade cellulose. See, e.g., Wood, 1985.

Cellulases are known in the art to be useful in the treatment of textiles for the purposes of enhancing the cleaning ability of detergent compositions, for use as a softening agent, for improving the feel and appearance of cotton fabrics, and the like (Kumar et al., 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,358,599; The Shizuoka Prefectural Hamamatsu Textile Industrial Research Institute Report, Vol. 24, pp. 54-61, 1986), have been described.

Hence, cellulases produced in fungi and bacteria have received significant attention. In particular, fermentation of *Trichoderma* spp. (e.g., *Trichoderma longibrachiatum* or *Trichoderma reesei*) has been shown to produce a complete cellulase system capable of degrading crystalline forms of cellulose. U.S. Pat. No. 5,475,101 discloses the purification and molecular cloning of one particularly useful enzyme designated EGIII which is derived from *Trichoderma longibrachiatum*.

Although cellulase compositions have been previously described, there remains a need for new and improved cellulase compositions for use in household detergents, stonewashing compositions or laundry detergents, etc. Cellulases that exhibit resistance to surfactants (e.g., linear alkyl sulfonates, LAS), improved performance under conditions of thermal stress, increased or decreased cellulolytic capacity, and/or high level expression in vitro, are of particular interest.

SUMMARY OF THE INVENTION

The invention provides an isolated cellulase protein, identified herein as BGL6, and nucleic acids which encode BGL6.

In one aspect, BGL6 polypeptides or proteins comprise a sequence having at least 80%, 85%, 90%, 95%, 98% or more sequence identity to the sequence presented as SEQ ID NO:2.

In a related aspect, the invention includes (i) fragments of BGL6, preferably at least about 20-100 amino acids in length, more preferably about 100-200 amino acids in length, and (ii) a pharmaceutical composition comprising BGL6. In various embodiments, the fragment corresponds to the N-terminal domain of BGL6 or the C-terminal domain of BGL6.

In another aspect the invention includes an isolated polynucleotide having a sequence which encodes BGL6, a sequence complementary to the bgl6 coding sequence, and a composition comprising the polynucleotide. The polynucleotide may be mRNA, DNA, cDNA, genomic DNA, or an antisense analog thereof.

A bgl6 polynucleotide may comprise an isolated nucleic acid molecule which hybridizes to the complement of the nucleic acid presented as SEQ ID NO: 1 under moderate to high stringency conditions, where the nucleic acid molecule encodes a BGL6 polypeptide that exhibits beta-glucosidase activity.

The polynucleotide may encode a BGL6 protein having at least 80%, 85%, 90%, 95%, 98% or more sequence identity to the sequence presented as SEQ ID NO:1. In a specific embodiment, the polynucleotide comprises a sequence substantially identical to SEQ ID NO:1. The invention also contemplates fragments of the polynucleotide, preferably at least about 15-30 nucleotides in length.

The invention further provides recombinant expression vectors containing a nucleic acid sequence encoding BGL6 or a fragment or splice variant thereof, operably linked to regulatory elements effective for expression of the protein in a selected host. In a related aspect, the invention includes a host cell containing the vector.

The invention further includes a method for producing BGL6 by recombinant techniques, by culturing recombinant prokaryotic or eukaryotic host cells comprising nucleic acid sequence encoding BGL6 under conditions effective to promote expression of the protein, and subsequent recovery of the protein from the host cell or the cell culture medium.

In another aspect the invention provides for an enzymatic composition useful in the conversion of cellulose to ethanol. In a preferred embodiment the enzymatic composition comprises BGL6. The composition may further comprise additional cellulase enzymes such as endoglucanases and/or cellobiohydrolases. The composition may be enriched in BGL6.

In yet another aspect, the invention includes an antibody specifically immunoreactive with BGL6.

Analytical methods for detecting bgl6 nucleic acids and BGL6 proteins also form part of the invention.

BRIEF DESCRIPTION OF THE FIGURES

FIGS. 1A and 1B show a single stranded depiction of the nucleic acid sequence (SEQ ID NO:1), of the *T. reesei* bgl6, wherein the non-coding sequence is indicated as underlined.

FIG. 2 shows the predicted amino acid sequence (SEQ ID NO:2) based on the nucleotide sequence provided in FIG. 1, wherein the first start codon is utilized.

FIG. 3 shows the predicted amino acid sequence (SEQ ID NO:4) based on the nucleotide sequence provided in FIG. 1, wherein the second start codon is utilized.

FIGS. 4A and 4B show the coding sequence bgl6 (SEQ ID NO:3), wherein the two alternate start codons are underlined.

DETAILED DESCRIPTION OF THE INVENTION

I. Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies which might be used in connection with the invention.

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

The term "nucleic acid molecule" includes RNA, DNA and cDNA molecules. It will be understood that, as a result of the degeneracy of the genetic code, a multitude of nucleotide sequences encoding a given protein such as BGL6 may be produced. The present invention contemplates every possible variant nucleotide sequence, encoding BGL6, all of which are possible given the degeneracy of the genetic code.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct used as a cloning vector, and which forms an extrachromosomal self-replicating genetic element in many bacteria and some eukaryotes.

As used herein, the term "selectable marker-encoding nucleotide sequence" refers to a nucleotide sequence which is capable of expression in cells and where expression of the selectable marker confers to cells containing the expressed gene the ability to grow in the presence of a corresponding selective agent, or under corresponding selective growth conditions.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

"Chimeric gene" or "heterologous nucleic acid construct", as defined herein refers to a non-native gene (i.e., one that has been introduced into a host) that may be composed of parts of different genes, including regulatory elements. A chimeric gene construct for transformation of a host cell is typically composed of a transcriptional regulatory region (promoter) operably linked to a heterologous protein coding sequence, or, in a selectable marker chimeric gene, to a selectable marker gene encoding a protein conferring antibiotic resistance to transformed cells. A typical chimeric gene of the present invention, for transformation into a host cell, includes a transcriptional regulatory region that is constitutive or inducible, a protein coding sequence, and a terminator sequence. A chimeric gene construct may also include a second DNA sequence encoding a signal peptide if secretion of the target protein is desired.

A nucleic acid is "operably linked" when it is placed into a functional relationship with another nucleic acid sequence. For example, DNA encoding a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors, linkers or primers for PCR are used in accordance with conventional practice.

As used herein, the term "gene" means the segment of DNA involved in producing a polypeptide chain, that may or may not include regions preceding and following the coding region, e.g. 5' untranslated (5' UTR) or "leader" sequences and 3' UTR or "trailer" sequences, as well as intervening sequences (introns) between individual coding segments (exons).

In general, nucleic acid molecules which encode BGL6 or an analog or homologue thereof will hybridize, under moderate to high stringency conditions to the sequence provided herein as SEQ ID NO:1. However, in some cases a BGL6-encoding nucleotide sequence is employed that possesses a substantially different codon usage, while the protein encoded by the BGL6-encoding nucleotide sequence has the same or substantially the same amino acid sequence as the native protein. For example, the coding sequence may be modified to facilitate faster expression of BGL6 in a particular prokaryotic or eukaryotic expression system, in accordance with the frequency with which a particular codon is utilized by the host. Te'o, et al. (2000), for example, describes the optimization of genes for expression in filamentous fungi.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "BGL6 expression" refers to transcription and translation of the bgl6 gene, the products of which include precursor RNA, mRNA, polypeptide, post-translationally processed polypeptides, and derivatives thereof, including BGL6 from related species such as *Trichoderma longibrachiatum* (reesei), *Trichoderma viride*, *Trichoderma koningii*, *Hypocrea jecorina* and *Hypocrea schweinitzii*. By way of example, assays for BGL6 expression include Western blot for BGL6 protein, Northern blot analysis and reverse transcriptase polymerase chain reaction (RT-PCR) assays for BGL6 mRNA, and glucosidase activity assays as described in Chen et al. (1992) and Herr et al. (1978).

The term "alternative splicing" refers to the process whereby multiple polypeptide isoforms are generated from a single gene, and involves the splicing together of nonconsecutive exons during the processing of some, but not all, transcripts of the gene. Thus a particular exon may be connected to any one of several alternative exons to form messenger RNAs. The alternatively-spliced mRNAs produce polypeptides ("splice variants") in which some parts are common while other parts are different.

The term "signal sequence" refers to a sequence of amino acids at the N-terminal portion of a protein which facilitates the secretion of the mature form of the protein outside the cell. The mature form of the extracellular protein lacks the signal sequence which is cleaved off during the secretion process.

By the term "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. In general, host cells are filamentous fungi.

The term "filamentous fungi" means any and all filamentous fungi recognized by those of skill in the art. A preferred fungus is selected from the group consisting of *Aspergillus, Trichoderma, Fusarium, Chrysosporium, Penicillium, Humicola, Neurospora*, or alternative sexual forms thereof such as *Emericella, Hypocrea*.

The term "cellooligosaccharide" refers to oligosaccharide groups containing from 2-8 glucose units and having β-1,4 linkages, e.g., cellobiose.

The term "cellulase" refers to a category of enzymes capable of hydrolyzing cellulose polymers to shorter cellooligosaccharide oligomers, cellobiose and/or glucose. Numerous examples of cellulases, such as exoglucanases, exocellobiohydrolases, endoglucanases, and glucosidases have been obtained from cellulolytic organisms, particularly including fungi, plants and bacteria.

The term "cellulose binding domain" as used herein refers to portion of the amino acid sequence of a cellulase or a region of the enzyme that is involved in the cellulose binding activity of a cellulase or derivative thereof. Cellulose binding domains generally function by non-covalently binding the cellulase to cellulose, a cellulose derivative or other polysaccharide equivalent thereof. Cellulose binding domains permit or facilitate hydrolysis of cellulose fibers by the structurally distinct catalytic core region, and typically function independent of the catalytic core. Thus, a cellulose binding domain will not possess the significant hydrolytic activity attributable to a catalytic core. In other words, a cellulose binding domain is a structural element of the cellulase enzyme protein tertiary structure that is distinct from the structural element which possesses catalytic activity.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "decrease or elimination in expression of the bgl6 gene" means that either that the bgl6 gene has been deleted from the genome and therefore cannot be expressed by the recombinant host microorganism; or that the bgl6 gene has been modified such that a functional BGL6 enzyme is not produced by the recombinant host microorganism.

The term "altered bgl6" or "altered bgl6 gene" means that the nucleic acid sequence of the gene has been altered by removing, adding, and/or manipulating the coding sequence or the amino acid sequence of the expressed protein has been modified.

As used herein, the term "purifying" generally refers to subjecting transgenic nucleic acid or protein containing cells to biochemical purification and/or column chromatography.

As used herein, the terms "active" and "biologically active" refer to a biological activity associated with a particular protein, such as the enzymatic activity associated with a protease. It follows that the biological activity of a given protein refers to any biological activity typically attributed to that protein by those of skill in the art.

As used herein, the term "enriched" means that the BGL6 is found in a concentration that is greater relative to the BGL6 concentration found in a wild-type, or naturally occurring, fungal cellulase composition.

A wild type fungal cellulase composition is one produced by a naturally occurring fungal source and which comprises one or more BG, CBH and EG components wherein each of these components is found at the ratio produced by the fungal source. Thus, an enriched BGL6 composition would have BGL6 at an altered ratio wherein the ratio of BGL6 to other cellulase components (i.e., CBHs and endoglucanases) is elevated. This ratio may be increased by either increasing BGL6 or decreasing (or eliminating) at least one other component by any means known in the art.

Thus, to illustrate, a naturally occurring cellulase system may be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. The purified BGL6 may then be added to the enzymatic solution resulting in an enriched BGL6 solution.

Fungal cellulases may contain more than one BG component. The different components generally have different isoelectric points which allow for their separation via ion exchange chromatography and the like. Either a single BG component or a combination of BG components may be employed in an enzymatic solution.

When employed in enzymatic solutions, the BG component is generally added in an amount sufficient to prevent inhibition by cellobiose of any CBH and endoglucanase components found in the cellulase composition. The amount of BG component added depends upon the amount of cellobiose produced during the biomass saccarification process which can be readily determined by the skilled artisan. However, when employed, the weight percent of the BGL6 component relative to any CBH or endoglucanase type components present in the cellulase composition is preferably from about 1, preferably about 5, preferably about 10, preferably about 15, or preferably about 20 weight percent to preferably about 25, preferably about 30, preferably about 35, preferably about 40, preferably about 45 or preferably about 50 weight percent. Furthermore, preferred ranges may be about 0.5 to about 15 weight percent, about 0.5 to about 20 weight percent, from about 1 to about 10 weight percent, from about 1 to about 15 weight percent, from about 1 to about 20 weight percent, from about 1 to about 25 weight percent, from about 5 to about 20 weight percent, from about 5 to about 25 weight percent, from about 5 to about 30 weight percent, from about 5 to about 35 weight percent, from about 5 to about 40 weight percent, from about 5 to about 45 weight percent, from about 5 to about 50 weight percent, from about 10 to about 20 weight percent, from about 10 to about 25 weight percent, from about 10 to about 30 weight percent, from about 10 to about 35 weight percent, from about 10 to about 40 weight percent, from about 10 to about 45 weight percent, from about 10 to about 50 weight percent, from about 15 to about 20 weight percent, from about 15 to about 25 weight percent, from about 15 to about 30 weight percent, from about 15 to about 35 weight percent, from about 15 to about 30 weight percent, from about 15 to about 45 weight percent, from about 15 to about 50 weight percent.

II. Target Organisms

A. Filamentous Fungi

Filamentous fungi include all filamentous forms of the subdivision Eumycota and Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic.

In the present invention, the filamentous fungal parent cell may be a cell of a species of, but not limited to, *Trichoderma*, e.g., *Trichoderma longibrachiatum* (reesei), *Trichoderma viride, Trichoderma koningii, Trichoderma harzianum; Penicillium* sp.; *Humicola* sp., including *Humicola insolens; Chrysosporium* sp., including *C. lucknowense; Gliocladium* sp.; *Aspergillus* sp.; *Fusarium* sp., *Neurospora* sp., *Hypocrea* sp., and *Emericella* sp. As used herein, the term "*Trichoderma*" or "*Trichoderma* sp." refers to any fungal strains which have previously been classified as *Trichoderma* or are currently classified as *Trichoderma*.

In one preferred embodiment, the filamentous fungal parent cell is an *Aspergillus niger, Aspergillus awamori, Aspergillus aculeatus*, or *Aspergillus nidulans* cell.

In another preferred embodiment, the filamentous fungal parent cell is a *Trichoderma reesei* cell.

III. Cellulases

Cellulases are known in the art as enzymes that hydrolyze cellulose (beta-1,4-glucan or beta D-glucosidic linkages) resulting in the formation of glucose, cellobiose, cellooligosaccharides, and the like. As set forth above, cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG"). (Knowles, et al., 1987; Schulein, 1988).

Certain fungi produce complete cellulase systems which include exocellobiohydrolases or CBH-type cellulases, endoglucanases or EG-type cellulases and beta-glucosidases or BG-type cellulases (Schulein, 1988). However, sometimes these systems lack CBH-type cellulases and bacterial cellulases also typically include little or no CBH-type cellulases. In addition, it has been shown that the EG components and CBH components synergistically interact to more efficiently degrade cellulose. See, e.g., Wood, 1985. The different components, i.e., the various endoglucanases and exocellobiohydrolases in a multi-component or complete cellulase system, generally have different properties, such as isoelectric point, molecular weight, degree of glycosylation, substrate specificity and enzymatic action patterns.

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exocellobiohydrolases by creating new chain ends which are recognized by exo-cellobiohydrolase components. Further, beta-glucosidase-type cellulases have been shown to catalyze the hydrolysis of alkyl and/or aryl β-D-glucosides such as methyl β-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Accordingly, β-glucosidase-type cellulases are considered to be an integral part of the cellulase system because they drive the overall reaction to glucose. Increased expression of BG in *T. reesei* has been shown to improve degradation of cellulose to glucose. See EP0562003, which is hereby incorporated by reference. In addition, (β-glucosidases can catalyze the hydrolysis of a number of different substrates, and therefore they find utility in a variety of different applications. Some β-glucosidases can be added to grapes during wine making to enhance the potential aroma of the finished wine product. Yet another application can be to use β-glucosidase in fruit to enhance the aroma thereof. Alternatively, β-glucosidase can be used directly in food additives or wine processing to enhance the flavor and aroma.

Cellulases also find a number of uses in detergent compositions including to enhance cleaning ability, as a softening agent and to improve the feel of cotton fabrics (Hemmpel, 1991; Tyndall, 1992; Kumar et al., 1997). While the mechanism is not part of the invention, softening and color restoration properties of cellulase have been attributed to the alkaline endoglucanase components in cellulase compositions, as exemplified by U.S. Pat. Nos. 5,648,263, 5,691,178, and 5,776,757, which disclose that detergent compositions containing a cellulase composition enriched in a specified alkaline endoglucanase component impart color restoration and improved softening to treated garments as compared to cellulase compositions not enriched in such a component. In addition, the use of such alkaline endoglucanase components in detergent compositions has been shown to complement the pH requirements of the detergent composition (e.g., by exhibiting maximal activity at an alkaline pH of 7.5 to 10, as described in U.S. Pat. Nos. 5,648,263, 5,691,178, and 5,776, 757).

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulose biomass to ethanol (wherein the cellulase degrades cellulose to glucose and yeast or other microbes further ferment the glucose into ethanol), in the treatment of mechanical pulp (Pere et al., 1996), for use as a feed additive (WO 91/04673) and in grain wet milling.

Numerous cellulases have been described in the scientific literature, examples of which include: from *Trichoderma reesei*: Shoemaker, S. et al., Bio/Technology, 1:691-696, 1983, which discloses CBHI; Teeri, T. et al., Gene, 51:43-52, 1987, which discloses CBHII; Penttila, M. et al., Gene, 45:253-263, 1986, which discloses EGI; Saloheimo, M. et al., Gene, 63:11-22, 1988, which discloses EGII; Okada, M. et al., Appl. Environ. Microbiol., 64:555-563, 1988, which discloses EGIII; Saloheimo, M. et al., Eur. J. Biochem., 249: 584-591, 1997, which discloses EGIV; Saloheimo, A. et al., Molecular Microbiology, 13:219-228, 1994, which discloses EGV; Barnett, C. C., et al., Bio/Technology, 9:562-567, 1991, which discloses BGL1, and Takashima, S. et al., J. Biochem., 125:728-736, 1999, which discloses BGL2. Cellulases from species other than *Trichoderma* have also been described e.g., Ooi et al., 1990, which discloses the cDNA sequence coding for endoglucanase F1-CMC produced by *Aspergillus aculeatus*; Kawaguchi T et al., 1996, which discloses the cloning and sequencing of the cDNA encoding beta-glucosidase 1 from *Aspergillus aculeatus*; Sakamoto et al., 1995, which discloses the cDNA sequence encoding the endoglucanase CMCase-1 from *Aspergillus kawachii* IFO 4308; Saarilahti et al., 1990 which discloses an endoglucanase from *Erwinia carotovara*; Spilliaert R, et al., 1994, which discloses the cloning and sequencing of bglA, coding for a thermostable beta-glucanase from *Rhodothermus marinu*; and Halldorsdottir S et al., 1998, which discloses the cloning, sequencing and overexpression of a *Rhodothermus marinus* gene encoding a thermostable cellulase of glycosyl hydrolase family 12. However, there remains a need for identification and characterization of novel cellulases, with improved properties, such as improved performance under conditions of thermal stress or in the presence of surfactants, increased specific activity, altered substrate cleavage pattern, and/or high level expression in vitro.

The development of new and improved cellulase compositions that comprise varying amounts CBH-type, EG-type and BG-type cellulases is of interest for use: (1) in detergent compositions that exhibit enhanced cleaning ability, function as a softening agent and/or improve the feel of cotton fabrics (e.g., "stone washing" or "biopolishing"); (2) in compositions for degrading wood pulp or other biomass into sugars (e.g., for bio-ethanol production); and/or (3) in feed compositions.

IV. Methods of Identifying Novel Sequences

Open reading frames (ORFs) are analyzed following full or partial sequencing of the *T. reesei* genome or of clones of cDNA libraries derived from *T. reesei* mRNA and are further analyzed using sequence analysis software, and by determining homology to known sequences in databases (public/private).

V. Bgl6 Nucleic Acids and BGL6 Polypeptides

A. Bgl6 Nucleic Acids

The nucleic acid molecules of the present invention include the native coding sequence, the cDNA sequence for bgl6 presented herein as SEQ. ID. NO:1, and homologues thereof in other species, naturally occurring allelic and splice variants, nucleic acid fragments, and biologically active (functional) derivatives thereof, such as, amino acid sequence variants of the native molecule and sequences which encode fusion proteins. The bgl6 gene has two putative start codons. The two start codons are underlined in FIG. 4. The sequences are collectively referred to herein as "BGL6-encoding nucleic acid sequences".

A Basic BLASTN search (ncbi.nlm.nih.gov/BLAST) of the non-redundant nucleic acid sequence database was conducted on Oct. 1, 2002, with the bgl6 gene sequence presented in FIG. 1 (SEQ ID NO:1), indicated that there were no sequences producing significant alignments (i.e. with an E value of $10^{-5}$ or less).

A bgl6 nucleic acid sequence of this invention may be a DNA or RNA sequence, derived from genomic DNA, cDNA, mRNA, or may be synthesized in whole or in part. The DNA may be double-stranded or single-stranded and if single-stranded may be the coding strand or the non-coding (antisense, complementary) strand. The nucleic acid sequence may be cloned, for example, by isolating genomic DNA from an appropriate source, and amplifying and cloning the sequence of interest using a polymerase chain reaction (PCR). Alternatively, nucleic acid sequence may be synthesized, either completely or in part, especially where it is desirable to provide host-preferred sequences for optimal expression. Thus, all or a portion of the desired structural gene (that portion of the gene which encodes a polypeptide or protein) may be synthesized using codons preferred by a selected host.

Due to the inherent degeneracy of the genetic code, nucleic acid sequences other than the native form which encode substantially the same or a functionally equivalent amino acid sequence may be used to clone and/or express BGL6-encoding nucleic acid sequences. Thus, for a given BGL6-encoding nucleic acid sequence, it is appreciated that as a result of the degeneracy of the genetic code, a number of coding sequences can be produced that encode a protein having the same amino acid sequence. For example, the triplet CGT encodes the amino acid arginine. Arginine is alternatively encoded by CGA, CGC, CGG, AGA, and AGG. Therefore it is appreciated that such substitutions in the coding region fall within the nucleic acid sequence variants covered by the present invention. Any and all of these sequence variants can be utilized in the same way as described herein for the native form of a BGL6-encoding nucleic acid sequence.

A "variant" BGL6-encoding nucleic acid sequence may encode a "variant" BGL6 amino acid sequence which is altered by one or more amino acids from the native polypeptide sequence or may be truncated by removal of one or more amino acids from either end of the polypeptide sequence, both of which are included within the scope of the invention. Similarly, the term "modified form of", relative to BGL6, means a derivative or variant form of the native BGL6 protein-encoding nucleic acid sequence or the native BGL6 amino acid sequence.

Similarly, the polynucleotides for use in practicing the invention include sequences which encode native BGL6 proteins and splice variants thereof, sequences complementary to the native protein coding sequence, and novel fragments of BGL6 encoding polynucleotides. A BGL6 encoding nucleic acid sequence may contain one or more intron sequences if it is a genomic DNA sequence.

In one general embodiment, a BGL6-encoding nucleotide sequence has at least 70%, preferably 80%, 85%, 90%, 95%, 98%, or more sequence identity to the bgl6 coding sequence presented herein as SEQ ID NO:1.

In another embodiment, a BGL6-encoding nucleotide sequence will hybridize under moderate to high stringency conditions to a nucleotide sequence that encodes a BGL6 protein. In a related embodiment, a BGL6-encoding nucleotide sequence will hybridize under moderate to high stringency conditions to the nucleotide sequence presented as SEQ ID NO:1.

It is appreciated that some nucleic acid sequence variants that encode BGL6 may or may not selectively hybridize to the parent sequence. By way of example, in situations where the coding sequence has been optimized based on the degeneracy of the genetic code, a variant coding sequence may be produced that encodes a BGL6 protein, but does not hybridize to a native BGL6-encoding nucleic acid sequence under moderate to high stringency conditions. This would occur, for example, when the sequence variant includes a different codon for each of the amino acids encoded by the parent nucleotide.

As will be further understood by those of skill in the art, in some cases it may be advantageous to produce nucleotide sequences possessing non-naturally occurring codons e.g., inosine or other non-naturally occurring nucleotide analog. Codons preferred by a particular eukaryotic host can be selected, for example, to increase the rate of BGL6 protein expression or to produce recombinant RNA transcripts having desirable properties, such as a longer half-life, than transcripts produced from the naturally occurring sequence. Hence, a native BGL6-encoding nucleotide sequence may be engineered in order to alter the coding sequence for a variety of reasons, including but not limited to, alterations which modify the cloning, processing and/or expression of the BGL6 protein by a cell.

Particularly preferred are nucleic acid substitutions, additions, and deletions that are silent such that they do not alter the properties or activities of the native polynucleotide or polypeptide.

The variations can be made using methods known in the art such as oligonucleotide-mediated (site-directed) mutagenesis, and PCR mutagenesis. Site-directed mutagenesis (Carter et al., 1986; Zoller et al., 1987), cassette mutagenesis (Wells et al., 1985), restriction selection mutagenesis (Wells et al., 1986) or other known techniques can be performed on the cloned DNA to produce the BGL6 polypeptide-encoding variant DNA.

However, in some cases it may be advantageous to express variants of bgl6 which lack the properties or activities of the native bgl6 polynucleotide or BGL6 polypeptide. In such cases, mutant or modified forms of the native BGL6-encoding nucleic acid sequence may be generated using techniques routinely employed by those of skill in the art.

B. BGL6 Polypeptides

In one preferred embodiment, the invention provides a BGL6 polypeptide, having a native mature or full-length BGL6 polypeptide sequence comprising the sequence presented in FIG. 2 (SEQ ID NO:2). A BGL6 polypeptide of the invention can be the mature BGL6 polypeptide, part of a fusion protein or a fragment or variant of the BGL6 polypeptide sequence presented in FIG. 2 (SEQ ID NO:2).

Ordinarily, a BGL6 polypeptide of the invention has at least 80% identity to a BGL6 amino acid sequence over its entire length. More preferable are BGL6 polypeptide sequences that comprise a region having at least 80, 85, 90, 95, 98% or more sequence identity to the BGL6 polypeptide sequence of FIG. 2 (SEQ ID NO:2), using a sequence alignment program, as detailed herein.

Typically, a "modified form of" a native BGL6 protein or a "variant" BGL6 protein has a derivative sequence containing at least one amino acid substitution, addition, deletion or insertion, respectively.

It is well-known in the art that certain amino acid substitutions may be made in protein sequences without affecting the function of the protein. Generally, conservative amino acid substitutions or substitutions of similar amino acids are tolerated without affecting protein function. Similar amino acids can be those that are similar in size and/or charge properties, for example, aspartate and glutamate, and isoleucine and valine, are both pairs of similar amino acids. Similarity between amino acid pairs has been assessed in the art in a number of ways. For example, Dayhoff et al. (1978), which is incorporated by reference herein provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Fragments and variants of the BGL6 polypeptide sequence of FIG. 2 (SEQ ID NO:2), are considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that are antigenic or immunogenic in an animal, particularly a human. In this aspect, the invention includes (i) fragments of BGL6, preferably at least about 20-100 amino acids in length, more preferably about 100-200 amino acids in length, and (ii) a pharmaceutical composition comprising BGL6. In various embodiments, the fragment corresponds to the N-terminal domain of BGL6 or the C-terminal domain of BGL6.

BGL6 polypeptides of the invention also include polypeptides that vary from the BGL6 polypeptide sequence of FIG. 2 (SEQ ID NO:2). These variants may be substitutional, insertional or deletional variants. The variants typically exhibit the same qualitative biological activity as the naturally occurring analogue, although variants can also be selected which have modified characteristics as further described below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of an isoleucine with a valine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). (See generally, Doolittle, R. F., 1986.)

A "non-conservative substitution" refers to the substitution of an amino acid in one class with an amino acid from another class.

BGL6 polypeptide variants typically exhibit the same qualitative biological activity as the naturally-occurring analogue, although variants also are selected to modify the characteristics of the BGL6 polypeptide, as needed. For example, glycosylation sites, and more particularly one or more O-linked or N-linked glycosylation sites may be altered or removed. Those skilled in the art will appreciate that amino acid changes may alter post-translational processes of the BGL6 polypeptide, such as changing the number or position of glycosylation sites or altering the membrane anchoring characteristics or secretion characteristics or other cellular localization characteristics.

Also included within the definition of BGL6 polypeptides are other related BGL6 polypeptides. Thus, probe or degenerate polymerase chain reaction (PCR) primer sequences may be used to find other related polypeptides. Useful probe or primer sequences may be designed to: all or part of the BGL6 polypeptide sequence, or sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of BGL6 polypeptides are also included within the scope of this invention. For example, the invention provides BGL6 polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of the protein from a precursor to a mature form, allow protein transport, shorten or lengthen protein half-life, or facilitate manipulation of the protein in assays or production. As an example, it is believed that the instant novel BGL6 polypeptide is an intracellular protein. Thus, in order to be exported to the extracellular milieu a secretion signal that is subsequently removed may be desirable.

Also contemplated are modifications directed to alteration of an active site, alteration of the pH optima, temperature optima, and/or substrate affinity of the BGL6 enzyme.

FIG. 2 shows the predicted amino acid sequence (SEQ ID NO:2) of an exemplary BGL6 polypeptide based on the nucleotide sequence provided in FIG. 1. The predicted molecular weight of the encoded BGL6 polypeptide is 92 kDa. No sequence resembling a signal peptide (Nielsen, H., Engelbrecht, J., Brunak, S., von Heijne, G., Protein Engineering, 10:1-6, 1997) is present at the amino terminus of BGL6 suggesting that the BGL6 polypeptide is not secreted.

A Basic BLASTP search (ncbi.nlm.nih.gov/BLAST) of the non-redundant protein database, conducted on Oct. 1, 2002 with the BGL6 amino acid sequence indicated 42% sequence identity to GenBank Accession Number P07337 (beta-glucosidase precursor of *Kluyveromyces marxianus* var. *marxianus*), 43% sequence identity to GenBank Accession Number AL355920 (beta-glucosidase precursor of *Schizosaccharomyces pombe*), 38% sequence identity to GenBank Accession Number AF329731 (beta-glucosidase of *Volvariella volvacea*), and 38% sequence identity to GenBank Accession Number AJ293760 (putative beta-glucosidase of *Agaricus bisporus*). The ten sequences having highest identity but less than 43% identity with BGL6 were all annotated as beta-glucosidases. These sequence similarities indicate that BGL6 is a member of glycosyl hydrolase family 3 (Henrissat, B. and Bairoch, A. (1993) Biochem. J. 293:781-788).

C. Anti-BGL6 Antibodies.

The present invention further provides anti-BGL6 antibodies. The antibodies may be polyclonal, monoclonal, humanized, bispecific or heteroconjugate antibodies.

Methods of preparing polyclonal antibodies are known to the skilled artisan. The immunizing agent may be a BGL6 polypeptide or a fusion protein thereof. It may be useful to conjugate the antigen to a protein known to be immunogenic in the mammal being immunized. The immunization protocol may be determined by one skilled in the art based on standard protocols or routine experimentation.

Alternatively, the anti-BGL6 antibodies may be monoclonal antibodies. Monoclonal antibodies may be produced by cells immunized in an animal or using recombinant DNA methods. (See, e.g., Kohler et al., 1975; U.S. Pat. No. 4,816,567).

An anti-BGL6 antibody of the invention may further comprise a humanized or human antibody. The term "humanized antibody" refers to humanized forms of non-human (e.g., murine) antibodies that are chimeric antibodies, immunoglobulin chains or fragments thereof (such as Fv, Fab, Fab', F(ab')$_2$ or other antigen-binding partial sequences of antibodies) which contain some portion of the sequence derived from non-human antibody. Methods for humanizing non-human antibodies are well known in the art, as further detailed in Jones et al., 1986; Riechmann et al., 1988; and Verhoeyen et al., 1988. Methods for producing human antibodies are also known in the art. See, e.g., Jakobovits, A, et al., 1995 and Jakobovits, A, 1995.

VI. Expression of Recombinant BGL6

The methods of the invention rely on the use cells to express BGL6, with no particular method of BGL6 expression required.

The invention provides host cells which have been transduced, transformed or transfected with an expression vector comprising a BGL6-encoding nucleic acid sequence. The culture conditions, such as temperature, pH and the like, are those previously used for the parental host cell prior to transduction, transformation or transfection and will be apparent to those skilled in the art.

In one approach, a filamentous fungal cell or yeast cell is transfected with an expression vector having a promoter or biologically active promoter fragment or one or more (e.g., a series) of enhancers which functions in the host cell line, operably linked to a DNA segment encoding BGL6, such that BGL6 is expressed in the cell line.

A. Nucleic Acid Constructs/Expression Vectors.

Natural or synthetic polynucleotide fragments encoding BGL6 ("BGL6-encoding nucleic acid sequences") may be incorporated into heterologous nucleic acid constructs or vectors, capable of introduction into, and replication in, a filamentous fungal or yeast cell. The vectors and methods disclosed herein are suitable for use in host cells for the expression of BGL6. Any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In:

Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related sub-cloning procedures are deemed to be within the scope of knowledge of those skilled in the art.

Recombinant filamentous fungi comprising the coding sequence for BGL6 may be produced by introducing a heterologous nucleic acid construct comprising the BGL6 coding sequence into the cells of a selected strain of the filamentous fungi.

Once the desired form of a bgl6 nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

A selected bgl6 coding sequence may be inserted into a suitable vector according to well-known recombinant techniques and used to transform filamentous fungi capable of BGL6 expression. Due to the inherent degeneracy of the genetic code, other nucleic acid sequences which encode substantially the same or a functionally equivalent amino acid sequence may be used to clone and express BGL6. Therefore it is appreciated that such substitutions in the coding region fall within the sequence variants covered by the present invention. Any and all of these sequence variants can be utilized in the same way as described herein for a parent BGL6-encoding nucleic acid sequence.

The present invention also includes recombinant nucleic acid constructs comprising one or more of the BGL6-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for bgl6, or a variant, fragment or splice variant thereof: (i) in isolation; (ii) in combination with additional coding sequences; such as fusion protein or signal peptide coding sequences, where the bgl6 coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the bgl6 coding sequence is a heterologous gene.

In one aspect of the present invention, a heterologous nucleic acid construct is employed to transfer a BGL6-encoding nucleic acid sequence into a cell in vitro, with established filamentous fungal and yeast lines preferred. For long-term, high-yield production of BGL6, stable expression is preferred. It follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Exemplary promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular filamentous fungus for expression purposes. It is operably linked to DNA sequence encoding a BGL6 polypeptide. Such linkage comprises positioning of the promoter with respect to the initiation codon of the DNA sequence encoding the BGL6 polypeptide in the disclosed expression vectors. The promoter sequence contains transcription and translation control sequence which mediate the expression of the BGL6 polypeptide. Examples include the promoters from the *Aspergillus niger, A. awamori* or *A. oryzae* glucoamylase, alpha-amylase, or alpha-glucosidase encoding genes; the *A. nidulans* gpdA or trpC genes; the *Neurospora crassa* cbh1 or trp1 genes; the *A. niger* or *Rhizomucor miehei* aspartic proteinase encoding genes; the *T. reesei* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *T. reesei*, amdS from *A. nidulans*, pyr4 from *Neurospora crassa* or *T. reesei*, pyrG from *Aspergillus niger* or *A. nidulans*. Additional exemplary selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *T. reesei* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Exemplary plasmids include pUC18, pBR322, and pUC100.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991. All patents, patent applications, articles and publications mentioned herein, are hereby expressly incorporated herein by reference.

B. Host Cells and Culture Conditions for Enhanced BGL6 Production (i) Filamentous Fungi Thus, the present invention provides filamentous fungi comprising cells which have been modified, selected and cultured in a manner effective to result in enhanced BGL6 production or expression relative to the corresponding non-transformed parental fungi.

Examples of species of parental filamentous fungi that may be treated and/or modified for enhanced BGL6 expression include, but are not limited to Trichoderma, e.g., Trichoderma reesei, Trichoderma longibrachiatum, Trichoderma viride, Trichoderma koningii; Penicillium sp., Humicola sp., including Humicola insolens; Aspergillus sp., Chrysosporium sp., Fusarium sp., Hypocrea sp., and Emericella sp.

BGL6 expressing cells are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Culture conditions are also standard, e.g., cultures are incubated at 28° C. in shaker cultures or fermenters until desired levels of BGL6 expression are achieved.

Preferred culture conditions for a given filamentous fungus may be found in the scientific literature and/or from the source of the fungi such as the American Type Culture Collection (ATCC; atcc.org). After fungal growth has been established, the cells are exposed to conditions effective to cause or permit the over expression of BGL6.

In cases where a BGL6 coding sequence is under the control of an inducible promoter, the inducing agent, e.g., a sugar, metal salt or antibiotics, is added to the medium at a concentration effective to induce high-level BGL6 expression.

(ii) Yeast

The present invention also contemplates the use of yeast as a host cell for BGL6 production. Several other genes encoding hydrolytic enzymes have been expressed in various strains of the yeast S. cerevisiae. These include sequences encoding for two endoglucanases (Penttila et al., 1987), two cellobiohydrolases (Penttila et al., 1988) and one beta-glucosidase from Trichoderma reesei (Cummings and Fowler, 1996), a xylanase from Aureobasidlium pullulans (Li and Ljungdahl, 1996), an alpha-amylase from wheat (Rothstein et al., 1987), etc. In addition, a cellulase gene cassette encoding the Butyrivibrio fibrisolvens endo-[beta]-1,4-glucanase (END1), Phanerochaete chrysosporium cellobiohydrolase (CBH 1), the Ruminococcus flavefaciens cellodextrinase (CEL1) and the Endomyces fibrifizer cellobiase (Bgl1) was successfully expressed in a laboratory strain of S. cerevisiae (Van Rensburg et al., 1998).

C. Introduction of a BGL6-Encodinq Nucleic Acid Sequence into Host Cells.

The invention further provides cells and cell compositions which have been genetically modified to comprise an exogenously provided BGL6-encoding nucleic acid sequence. A parental cell or cell line may be genetically modified (i.e., transduced, transformed or transfected) with a cloning vector or an expression vector. The vector may be, for example, in the form of a plasmid, a viral particle, a phage, etc, as further described above.

Various methods may be employed for delivering an expression vector into cells in vitro. After a suitable vector is constructed, it is used to transform strains of fungi or yeast. General methods of introducing nucleic acids into cells for expression of heterologous nucleic acid sequences are known to the ordinarily skilled artisan. Such methods include, but not limited to, electroporation; nuclear microinjection or direct microinjection into single cells; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; and the like.

Preferred methods for introducing a heterologous nucleic acid construct (expression vector) into filamentous fungi (e.g., T. reesei) include, but are not limited to the use of a particle or gene gun, permeabilization of filamentous fungi cells walls prior to the transformation process (e.g., by use of high concentrations of alkali, e.g., 0.05 M to 0.4 M $CaCl_2$ or lithium acetate), protoplast fusion or agrobacterium mediated transformation. An exemplary method for transformation of filamentous fungi by treatment of protoplasts or spheroplasts with polyethylene glycol and $CaCl_2$ is described in Campbell, E. I. et al., Curr. Genet. 16:53-56, 1989 and Penttila, M. et al., Gene, 63:11-22, 1988.

In addition, heterologous nucleic acid constructs comprising a BGL6-encoding nucleic acid sequence can be transcribed in vitro, and the resulting RNA introduced into the host cell by well-known methods, e.g., by injection.

Following introduction of a heterologous nucleic acid construct comprising the coding sequence for bgl6, the genetically modified cells can be cultured in conventional nutrient media modified as appropriate for activating promoters, selecting transformants or amplifying expression of a BGL6-encoding nucleic acid sequence. The culture conditions, such as temperature, pH and the like, are those previously used for the host cell selected for expression, and will be apparent to those skilled in the art.

The progeny of cells into which such heterologous nucleic acid constructs have been introduced are generally considered to comprise the BGL6-encoding nucleic acid sequence found in the heterologous nucleic acid construct.

The invention further includes novel and useful transformants of filamentous fungi such as Trichoderma reesei for use in producing fungal cellulase compositions. The invention includes transformants of filamentous fungi especially fungi comprising the bgl6 coding sequence, comprising a modified form of the bgl6 coding sequence or deletion of the bgl6 coding sequence.

Stable transformants of filamentous fungi can generally be distinguished from unstable transformants by their faster growth rate and the formation of circular colonies with a smooth rather than ragged outline on solid culture medium. Additionally, in some cases, a further test of stability can be made by growing the transformants on solid non-selective medium, harvesting the spores from this culture medium and determining the percentage of these spores which will subsequently germinate and grow on selective medium.

VII. Analysis for BGL6 Nucleic Acid Coding Sequences and/or Protein Expression

In order to evaluate the expression of BGL6 by a cell line that has been transformed with a BGL6-encoding nucleic acid construct, assays can be carried out at the protein level, the RNA level or by use of functional bioassays particular to glucosidase activity and/or production.

In one exemplary application of the bgl6 nucleic acid and protein sequences described herein, a genetically modified strain of filamentous fungi, e.g., Trichoderma reesei, is engineered to produce an increased amount of BGL6. Such genetically modified filamentous fungi would be useful to produce a cellulase product with greater increased cellulolytic capacity. In one approach, this is accomplished by introducing the coding sequence for bgl6 into a suitable host, e.g., a filamentous fungi such as Trichoderma reesei.

Accordingly, the invention includes methods for expressing BGL6 in a filamentous fungus or other suitable host by introducing an expression vector containing the DNA sequence encoding BGL6 into cells of the filamentous fungus or other suitable host.

In another aspect, the invention includes methods for modifying the expression of BGL6 in a filamentous fungus or other suitable host. Such modification includes a decrease or elimination in expression, or expression of an altered form of BGL6. An altered form of BGL6 may have an altered amino acid sequence or an altered nucleic acid sequence.

In general, assays employed to analyze the expression of BGL6 include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of BGL6 may be measured in a sample directly, for example, by assays for glucosidase activity, expression and/or production. Such assays are described, for example, in Chen et al. (1992), Herr et al. (1978), and U.S. Pat. No. 6,184,018 (Li et al.; 2001), each of which is expressly incorporated by reference herein. The ability of BGL6 to hydrolyze isolated soluble and insoluble substrates can be measured using assays described in Suurnakki et al. (2000) and Ortega et al. (2001). Substrates useful for assaying cellobiohydrolase, endoglucanase or β-glucosidase activities include crystalline cellulose, filter paper, phosphoric acid swollen cellulose, hydroxyethyl cellulose, carboxymethyl cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside, orthonitrophenyl glucoside, paranitrophenyl glucoside, methylumbelliferyl glycoside. The latter three are particularly useful in assaying β-glucosidases. β-glucosidase assays are well-known in the art. See Cummings and Fowler (1996).

In addition, protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of BGL6. The details of such methods are known to those of skill in the art and many reagents for practicing such methods are commercially available.

A purified form of BGL6 may be used to produce either monoclonal or polyclonal antibodies specific to the expressed protein for use in various immunoassays. (See, e.g., Hu et al., 1991). Exemplary assays include ELISA, competitive immunoassays, radioimmunoassays, Western blot, indirect immunofluorescent assays and the like. In general, commercially available antibodies and/or kits may be used for the quantitative immunoassay of the expression level of glucosidase proteins.

VIII. Isolation and Purification of Recombinant BGL6 Protein

In general, a BGL6 protein produced in cell culture is secreted into the medium and may be purified or isolated, e.g., by removing unwanted components from the cell culture medium. However, in some cases, a BGL6 protein may be produced in a cellular form necessitating recovery from a cell lysate. In such cases the BGL6 protein is purified from the cells in which it was produced using techniques routinely employed by those of skill in the art. Examples include, but are not limited to, affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

Typically, the BGL6 protein is fractionated to segregate proteins having selected properties, such as binding affinity to particular binding agents, e.g., antibodies or receptors; or which have a selected molecular weight range, or range of isoelectric points.

Once expression of a given BGL6 protein is achieved, the BGL6 protein thereby produced is purified from the cells or cell culture. Exemplary procedures suitable for such purification include the following: antibody-affinity column chromatography, ion exchange chromatography; ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75. Various methods of protein purification may be employed and such methods are known in the art and described e.g. in Deutscher, 1990; Scopes, 1982. The purification step(s) selected will depend, e.g., on the nature of the production process used and the particular protein produced.

IX. Utility of bgl6 and BGL6

It can be appreciated that the bgl6 nucleotide, the BGL6 protein and compositions comprising BGL6 protein activity find utility in a wide variety applications, some of which are described below.

New and improved cellulase compositions that comprise varying amounts CBH-type, EG-type and BG-type cellulases find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of cellulase of each type provides the ability to control the aspects of such compositions.

In one preferred approach, the cellulase of the invention finds utility in detergent compositions or in the treatment of fabrics to improve the feel and appearance.

The inventive β-glucosidases can be used in a variety of different applications. For example, the β-glucosidase may be added to grapes during wine making to enhance the potential aroma of the finished wine product. Yet another application can be to use β-glucosidase in fruit to enhance the aroma thereof. Alternatively, the isolated recombinant fermentation product containing enhanced β-glucosidase can be used directly in food additives or wine processing to enhance the flavor or aroma.

Since the rate of hydrolysis of cellulosic products may be increased by using a transformant having at least one additional copy of the bgl6 gene inserted into the genome, products that contain cellulose or heteroglycans can be degraded at a faster rate and to a greater extent. Products made from cellulose such as paper, cotton, cellulosic diapers and the like can be degraded more efficiently in a landfill. Thus, the fermentation product obtainable from the transformants or the transformants alone may be used in compositions to help degrade by liquefaction a variety of cellulose products that add to the overcrowded landfills.

Separate saccharification and fermentation is a process cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another preferred approach, the glucosidase type cellulase of the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the inventive β-glucosidase and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

A cellulase composition containing an enhanced amount of β-glucosidase finds utility in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Ethanol can be produced via saccharification and fermentation processes from cellulosic biomass such as trees, herbaceous plants, municipal solid waste and agricultural and forestry residues. However, one major problem encountered in this process is the lack of β-glucosidase in the system to convert cellobiose to glucose. It is known that cellobiose acts as an inhibitor of cellobiohydrolases and endoglucanases and thereby reduces the rate of hydrolysis for the entire cellulase system. Therefore, the use of increased β-glucosidase activity to quickly convert cellobiose into glucose would greatly enhance the production of ethanol.

Thus, the inventive β-glucosidase finds use in the hydrolysis of cellulose to its sugar components. In one embodiment, the β-glucosidase is added to the biomass prior to the addition of a fermentative organism. In a second embodiment, the β-glucosidase is added to the biomass at the same time as a fermentative organism. Optionally, there may be other cellulase components present in either embodiment.

In another embodiment the cellulosic feedstock may be pretreated. Pretreatment may be by elevated temperature and the addition of either of dilute acid, concentrated acid or dilute alkali solution. The pretreatment solution is added for a time sufficient to at least partially hydrolyze the hemicellulose components and then neutralized.

In an alternative approach, a cellulase composition which is deficient in or free of β-glucosidase is preferred. The deletion of the β-glucosidase gene of this invention would be particularly useful in preparing cellulase compositions for use in detergents. Additionally, such compositions are useful for the production of cellobiose and other cellooligosaccharides. The deletion of the bgl6 gene from *T. reesei* strains would be particularly useful in preparing cellulase compositions for use in the detergents and in isolating cellobiose. The cellulase enzymes have been used in a variety of detergent compositions to enzymatically clean clothes. However, it is known in this art that use of cellulase enzymes can impart degradation of the cellulose fibers in clothes. One possibility to decrease the degradation effect is to produce a detergent that does not contain β-glucosidase. Thus, the deletion of this protein would effect the cellulase system to inhibit the other components via accumulation of cellobiose. The modified microorganisms of this invention are particularly suitable for preparing such compositions because the bgl6 gene can be deleted leaving the remaining CBH and EG components resulting in improved cleaning and softening benefits in the composition without degradative effects.

The detergent compositions of this invention may employ besides the cellulase composition (irrespective of the β-glucosidase content, i.e., β-glucosidase-free, substantially β-glucosidase-free, or β-glucosidase enhanced), a surfactant, including anionic, non-ionic and ampholytic surfactants, a hydrolase, building agents, bleaching agents, bluing agents and fluorescent dyes, caking inhibitors, solubilizers, cationic surfactants and the like. All of these components are known in the detergent art. The cellulase composition as described above can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent. For a more thorough discussion, see U.S. Pat. No. 6,162,782 entitled "Detergent compositions containing cellulase compositions deficient in CBH I type components," which is incorporated herein by reference.

In yet another embodiment, the detergent compositions can also contain enhanced levels of beta-glucosidase or altered beta-glucosidase. In this regard, it really depends upon the type of product one desires to use in detergent compositions to give the appropriate effects.

Preferably the cellulase compositions are employed from about 0.00005 weight percent to about 5 weight percent relative to the total detergent composition. More preferably, the cellulase compositions are employed from about 0.0002 weight percent to about 2 weight percent relative to the total detergent composition.

Deletion of the bgl6 gene would also provide accumulation of cellobiose in the cellulase system, which can be purified therefrom. In this regard, the present invention presents the possibility to isolate cellobiose from microorganisms in an easy and effective manner.

Portions of the bgl6 nucleic acid sequence that are capable of binding to cellulose can be used to generate bacterial chimeric surface proteins, allowing whole-cell immobilization onto cellulose filters or other fibrous solid supports as described in Lehtio et al., 2001.

In addition the bgl6 nucleic acid sequence finds utility in the identification and characterization of related nucleic acid sequences. A number of techniques useful for determining (predicting or confirming) the function of related genes or gene products include, but are not limited to, (A) DNA/RNA analysis, such as (1) overexpression, ectopic expression, and expression in other species; (2) gene knock-out (reverse genetics, targeted knock-out, viral induced gene silencing (VIGS, see Baulcombe, 1999); (3) analysis of the methylation status of the gene, especially flanking regulatory regions; and (4) in situ hybridization; (B) gene product analysis such as (1) recombinant protein expression; (2) antisera production, (3) immunolocalization; (4) biochemical assays for catalytic or other activity; (5) phosphorylation status; and (6) interaction with other proteins via yeast two-hybrid analysis; (C) pathway analysis, such as placing a gene or gene product within a particular biochemical or signaling pathway based on its overexpression phenotype or by sequence homology with related genes; and (D) other analyses which may also be performed to determine or confirm the participation of the isolated gene and its product in a particular metabolic or signaling pathway, and help determine gene function.

Endoglucanases and beta-glucosidases may be responsible for the production of disaccharides, such as sophorose, from cellooligosaccharides and glucose by transglycosylation reactions. Sophorose is known to be a very potent inducer of cellulase gene expression (Ilmen, M. et al., 1997, Appl. Environ. Microbiol. 63:1298-1306 and references therein). In this way EGs and BGLs may play an important role in the process of induction of cellulase gene expression. Over-expression of certain EGs or BGLs in a fungal strain may lead to higher overall cellulase productivity by that strain.

A. Homology to Known Sequences

The function of a related BGL6-encoding nucleic acid sequence may be determined by homology to known genes having a particular function. For example, a comparison of the coding sequence of an identified nucleic acid molecule to public nucleic acid sequence databases is used to confirm function by homology to known genes or by extension of the identified nucleic acid sequence.

The term "% homology" is used interchangeably herein with the term "% identity" herein and refers to the level of nucleic acid or amino acid sequence identity between the nucleic acid sequence that encodes BGL6 or the BGL6 amino acid sequence, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence, e.g., the coding sequence for bgl6, as described herein.

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet at ncbi.nlm.nih.gov/BLAST. See also, Altschul, et al., 1990 and Altschul, et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences that have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. (See, e.g., Altschul, et al., 1997.)

A preferred alignment of selected sequences in order to determine "% identity" between two or more sequences, is performed using for example, the CLUSTAL-W program in MacVector version 6.5, operated with default parameters, including an open gap penalty of 10.0, an extended gap penalty of 0.1, and a BLOSUM 30 similarity matrix.

In one exemplary approach, sequence extension of a nucleic acid encoding bgl6 may be carried out using conventional primer extension procedures as described in Sambrook et al., supra, to detect bgl6 precursors and processing intermediates of mRNA that may not have been reverse-transcribed into cDNA and/or to identify ORFs that encode a full length protein.

In yet another aspect, the present invention includes the entire or partial nucleotide sequence of the nucleic acid sequence of bgl6 for use as a probe. Such a probe may be used to identify and clone out homologous nucleic acid sequences from related organisms.

Screening of a cDNA or genomic library with the selected probe may be conducted using standard procedures, such as described in Sambrook et al., (1989). Hybridization conditions, including moderate stringency and high stringency, are provided in Sambrook et al., supra.

The probes or portions thereof may also be employed in PCR techniques to generate a pool of sequences for identification of closely related bgl6 sequences. When bgl6 sequences are intended for use as probes, a particular portion of a BGL6 encoding sequence, for example a highly conserved portion of the coding sequence may be used.

For example, a bgl6 nucleotide sequence may be used as a hybridization probe for a cDNA library to isolate genes, for example, those encoding naturally-occurring variants of BGL6 from other fungal, bacterial or plant species, which have a desired level of sequence identity to the bgl6 nucleotide sequence disclosed in FIG. 1 (SEQ ID NO:1). Exemplary probes have a length of about 20 to about 50 bases.

B. Two Hybrid Analysis

Proteins identified by the present invention can be used in the yeast two-hybrid system to "capture" protein binding proteins which are putative signal pathway proteins. The yeast two hybrid system is described in Fields and Song, *Nature* 340:245-246 (1989). Briefly, in a two-hybrid system, a fusion of a DNA-binding domain-bgl6 (e.g., GAL4-bgl6 fusion) is constructed and transfected into yeast cells. The whole bgl6 gene, or subregions of the bgl6 gene, may be used. A second construct containing the library of potential binding partners fused to the DNA activation domain is co-transfected. Yeast co-transformants harboring proteins that bind to the BGL6 protein are identified by, for example, beta-galactosidase or luciferase production (a screen), or survival on plates lacking an essential nutrient (a selection), as appropriate for the vectors used.

C. Microarray Analysis

In addition, microarray analysis, also known as expression profiling or transcript profiling, may be used to simultaneously evaluate the presence or expression of given DNA sequences, or changes in the expression of many different genes. In one approach, a large set of DNA sequences (probes), usually a broad set of expressed sequence tags, cDNAs, cDNA fragments, or sequence-specific oligonucleotides, is arrayed on a solid support such as a glass slide or nylon membrane. Labelled target for hybridization to the probes is generated by isolating mRNA from control and induced tissue, then labeling each mRNA pool either directly or via a cDNA or cRNA intermediate, with a distinct marker, usually a fluorescent dye. The microarray is hybridized with the complex probes, and the relative hybridization signal intensity associated with each location on the array can be quantitated for each marker dye. Differences in expression between the control and induced states can be measured as a ratio of the signal from the two marker dyes. (See Baldwin, D et al., 1999.)

Microarray analysis of the source organism from which bgl6 was derived may be carried out, to facilitate the understanding of gene function by identifying other genes that are coordinately regulated as a consequence of the overexpression of bgl6. The identity of coordinately regulated genes may help to place the bgl6 gene in a particular pathway. Alternatively, such analysis may be used to identify other genes involved in the same pathway using microarray analysis.

All publications, patents and patent applications are herein expressly incorporated by reference in their entirety.

While the invention has been described with reference to specific methods and embodiments, it will be appreciated that various modifications and changes may be made without departing from the invention.

EXAMPLE 1

In one exemplary approach, a cDNA fragment for use as a probe is isolated by extracting total RNA from mycelia of a *T. reesei* strain grown under conditions known to induce cellulase production and obtaining the polyadenylated (polyA) fraction therefrom. The polyA RNA is used to produce a cDNA pool which is then amplified using specific primers based on the bgl6 nucleic acid sequence provided herein.

Total RNA is isolated from the mycelia using methods known in the art, for example as described in Timberlake et al., 1981; Maniatis, et al., 1989; Ausubel, et al., 1993 and Sambrook et al., 1989, each of which is expressly incorporated by reference herein. Once isolated, Northern blots are performed to confirm cellulase expression and select an optimal induction time for cellulase expression and corresponding RNA isolation.

Messenger RNA (mRNA), having a poly (A) tail at the 3' end, may be purified from total RNA using methods known in the art.

The *T. reesei* RNA is used as template for RT-PCR using methods known in the art (Loftus, J. et al., Science, 249:915-918, 1990). During this procedure the mRNA is reverse transcribed to produce first strand cDNA. The cDNA subsequently serves as template for PCR amplification of bgl6 cDNA sequences using specific olionucleotide primers designed in accordance with SEQ ID No. 1 or SEQ ID No. 3.

TABLE 1

Sequences Provided In Support Of The Invention.

| Description | SEQ. ID NO. |
|---|---|
| full length bgl6 DNA nucleic acid sequence | 1 |

GATCACACCCCTCCCACCCTTCTCTTTTCAAGGTTGTCCCCTTCTCCCAC

GGCTTTATGTACTTCCCACTCTMTAATTCGCTCTTTCCATTCCAAGCCAAG

CAACATCTGTGAGCAGCTCATCCTTCCCAATATGGGCGAATGGCAGGAG

CAGATGATGGGTTTTGACGTGGAGGATGTTCTGTCTCAGCTGAGCCAAAA

TGAGAAGATTGCTCTCTTGTCCGGCATTGATTTCTGGCATACTTATCCCAT

ACCAAAGTACAACGTCCCTTCAGTCCGCCTAACGGACGGTCCTAACGGC

ATACGAGGCACAAAGTTTTTTGCTGGCATTCCTGCTGCCTGCCTGCCATG

TGGGACGGCCCTGGCCTCTACCTGGGATAAGCAGCTGCTGAAGAAGGCT

GGGAAGCTGCTCGGTGATGAGTGCATCGCAAAAGGCGCCCACTGCTGG

CTGGGCCCAACAATCAATACTCCCCGATCTCCTCTGGGGGGCGCGGCT

TCGAGTCATTTTCGGAAGATCCGTACCTGTCCGGCATCCTTGCTGCATCT

ATGATTCTCGGCTGTGAAAGCACAGGTGTCATCTCTGCCGTCAAACACTT

TGTCGCCAACGACCAGGAGCACGAGCGGCGAGCGGTCGACTGTCTCAT

CACCCAGCGGGCTCTCCGGGAGGTCTATCTGCGACCCTTCCAGATCGTA

GCCCGAGATGCAAGGCCCGGCGCATTGATGACATCCTACAACAAGGTCA

ATGGCAAGCACGTCGCTGACAGCGCCGAGTTCCTTCAGGGCATTCTCCG

GACTGAGTGGAATTGGGATCCTCTCATTGTCAGCGACTGGTACGGCACC

TACACCACTATTGATGCCATCAAAGCCGGCCTTGATCTCGAGATGCCGGG

CGTTTCACGATATCGCGGCAAATACATCGAGTCTGCTCTGCAGGCCCGTT

TG CTGAAGCAGTCCACTATCGATGAGCGCGCTCGCCGCGTGCTCAGGTT

CGCCCAGAAGGCCAGCCATCTCAAGGTCTCCGAGGTAGAGCAAGGCCGT

GACTTCCCAGAGGATCGCGTCCTCAACCGTCAGATCTGCGGCAGCAGCA

TTGTCCTACTGAAGAATGAGAACTCCATCTTACCTCTCCCCAAGTCCGTC

AAGAAGGTCGCCCTTGTTGGATCCCACGTGCGTCTACCGGCTATCTCGG

TABLE 1-continued

Sequences Provided In Support Of The Invention.

| Description | SEQ. ID NO. |
|---|---|
| GAGGAGGCAGCGCCTCTCTTGTCCCTTACTATGCCATATCTCTATACGAT | |
| GCCGTCTCTGAGGTACTAGCCGGTGCCACGATCACGCACGAGGTCGGTG | |
| CCTATGCCCACCAAATGCTGCCCGTCATCGACGCAATGATCAGCAACGC | |
| CGTAATCCACTTCTACAACGACCCCATCGATGTCAAAGACAGAAAGCTCC | |
| TTGGCAGTGAGAACGTATCGTCGACATCGTTCCAGCTCATGGATTACAAC | |
| AACATCCCAACGCTCAACAAGGCCATGTTCTGGGGTACTCTCGTGGGCG | |
| AGTTTATCCCTACCGCCACGGGAATTTGGGAATTTGGCCTCAGTGTCTTT | |
| GGCACTGCCGACCTTTATATTGATAATGAGCTCGTGATTGAAAATACAACA | |
| CATCAGACGCGTGGTACCGCCTTTTTCGGAAAGGGAACGACGGAAAAAG | |
| TCGCTACCAGGAGGATGGTGGCCGGCAGCACCTACAAGCTGCGTCTCGA | |
| GTTTGGGTCTGCCAACACGACCAAGATGGAGACGACCGGTGTTGTCAAC | |
| TTTGGCGGCGGTGCCGTACACCTGGGTGCCTGTCTCAAGGTCGACCCAC | |
| AGGAGATGATTGCGCGGGCCGTCAAGGCCGCAGCCGATGCCGACTACA | |
| CCATCATCTGCACGGGACTCAGCGGCGAGTGGGAGTCTGAGGGTTTTGA | |
| CCGGCCTCACATGGACCTGCCCCCTGGTGTGGACACCATGATCTCGCAA | |
| GTTCTTGACGCCGCTCCCAATGCTGTAGTCGTCAACCAGTCAGGCACCC | |
| CAGTGACAATGAGCTGGGCTCATAAAGCAAAGGCCATTGTGCAGGCTTG | |
| GTATGGTGGTAACGAGACAGGCCACGGAATCTCCGATGTGCTCTTTGGC | |
| AACGTCAACCCGTCGGGGAAACTCTCCCTATCGTGGCCAGTCGATGTGA | |
| AGCACAACCCAGCATATCTCAACTACGCCAGCGTTGGTGGACGGGTCTT | |
| GTATGGCGAGGATGTTTACGTTGGCTACAAGTTCTACGACAAAACGGAGA | |
| GGGAGGTTCTGTTTCCTTTTGGGCATGGCCTGTCTTACGCTACCTTCAAG | |
| CTCCCAGATTCTACCGTGAGGACGGTCCCCGAAACCTTCCACCCGGACC | |
| AGCCCACAGTAGCCATTGTCAAGATCAAGAACACGAGCAGTGTCCCGGG | |
| CGCCCAGGTCCTGCAGCTATACATTTCGGCCCCAAACTCGCCTACACATC | |
| GCCCGGTCAAGGAGCTGCACGGATTCGAAAAGGTGTATCTTGAAGCTGG | |
| CGAGGAGAAGGAGGTACAAATACCCATTGACCAGTACGCTACTAGCTTCT | |
| GGGACGAGATTGAGAGCATGTGGAAGAGCGAGAGGGGCATTTATGATGT | |
| GCTTGTAGGATTCTCGAGTCAGGAAATCTCGGGCAAGGGGAAGCTGATT | |
| GTGCCTGAAACGCGATTCTGGATGGGGCTGTAG<ins>ATTCAACACGTGAGCA</ins> | |
| <ins>AAAGCGATTGCGGAAAGTACCAGAAAAGCCAAGGGAGTCAAAGGATGGG</ins> | |
| <ins>AACTTGTGTCAATAGAAGATATGCATAGATGGGCATTCTGGGATGGTGGT</ins> | |
| <ins>TTGGCATTAATGCAAAGAAGACAAAGATGGATGTGATAAAAAAAAAAAAA</ins> | |
| <ins>AAAAA</ins> | |
| BGL6 predicted amino acid sequence<br>MGEWQEQMMGFDVEDVLSQLSQNEKIALLSGIDFWHTYPIPKYNVPSVRLT | 2 |
| DGPNGIRGTKFFAGIPAACLPCGTALASTWDKQLLKKAGKLLGDECIAKGAH | |
| CWLGPTINTPRSPLGGRGFESFSEDPYLSGILAASMILGCESTGVISAVKHFV | |

TABLE 1-continued

Sequences Provided In Support Of The Invention.

| Description | SEQ. ID NO. |
|---|---|
| ANDQEHERRAVDCLITQRALREVYLRPFQIVARDARPGALMTSYNKVNGKHV | |
| ADSAEFLQGILRTEWNWDPLIVSDWYGTYTTIDAIKAGLDLEMPGVSRYRGK | |
| YIESALQARLLKQSTIDERARRVLRFAQKASHLKVSEVEQGRDFPEDRVLNR | |
| QICGSSIVLLKNENSILPLPKSVKKVALVGSHVRLPAISGGGSASLVPYYAISLY | |
| DAVSEVLAGATITHEVGAYAHQMLPVIDAMISNAVIHFYNDPIDVKDRKLLGSE | |
| NVSSTSFQLMDYNNIPTLNKAMFWGTLVGEFIPTATGIWEFGLSVFGTADLYI | |
| DNELVIENTTHQTRGTAFFGKGTTEKVATRRMVAGSTYKLRLEFGSANTTKM | |
| ETTGVVNFGGGAVHLGACLKVDPQEMIARAVKAAADADYTIICTGLSGEWES | |
| EGFDRPHMDLPPGVDTMISQVLDAAPNAVVVNQSGTPVTMSWAHKAKAIVQ | |
| AWYGGNETGHGISDVLFGNVNPSGKLSLSWPVDVKHNPAYLNYASVGGRV | |
| LYGEDVYVGYKFYDKTEREVLFPFGHGLSYATFKLPDSTVRTVPETFHPDQP | |
| TVAIVKIKNTSSVPGAQVLQLYISAPNSPTHRPVKELHGFEKVYLEAGEEKEV | |
| QIPIDQYATSFWDEIESMWKSERGIYDVLVGFSSQEISGKGKLIVPETRFWMG | |
| L | |
| BGL6 predicted amino acid sequence with alternate start MMGFDVEDVLSQLSQNEKIALLSGIDFWHTYPIPKYNVPSVRLTDGPNGIRGT | 4 |
| KFFAGIPAACLPCGTALASTWDKQLLKKAGKLLGDECIAKGAHCWLGPTINTP | |
| RSPLGGRGFESFSEDPYLSGILAASMILGCESTGVISAVKHFVANDQEHERR | |
| AVDCLITQRALREVYLRPFQIVARDARPGALMTSYNKVNGKHVADSAEFLQGI | |
| LRTEWNWDPLIVSDWYGTYTTIDAIKAGLDLEMPGVSRYRGKYIESALQARLL | |
| KQSTIDERARRVLRFAQKASHLKVSEVEQGRDFPEDRVLNRQICGSSIVLLKN | |
| ENSILPLPKSVKKVALVGSHVRLPAISGGGSASLVPYYAISLYDAVSEVLAGAT | |
| ITHEVGAYAHQMLPVIDAMISNAVIHFYNDPIDVKDRKLLGSENVSSTSFQLM | |
| DYNNIPTLNKAMFWGTLVGEFIPTATGIWEFGLSVFGTADLYIDNELVIENTTH | |
| QTRGTAFFGKGTTEKVATRRMVAGSTYKLRLEFGSANTTKMETTGVVNFGG | |
| GAVHLGACLKVDPQEMIARAVKAAADADYTIICTGLSGEWESEGFDRPHMDL | |
| PPGVDTMISQVLDAAPNAVVVNQSGTPVTMSWAHKAKAIVQAWYGGNETG | |
| FIGISDVLFGNVNPSGKLSLSWPVDVKHNPAYLNYASVGGRVLYGEDVYVGY | |
| KFYDKTEREVLFPFGHGLSYATFKLPDSTVRTVPETFHPDQPTVAIVKIKNTS | |
| SVPGAQVLQLYISAPNSPTHRPVKELHGFEKVYLEAGEEKEVQIPIDQYATSF | |
| WDEIESMWKSERGIYDVLVGFSSQEISGKGKLIVPETRFWMGL | |
| bgl6 nucleic acid coding sequence<br><u>ATG</u>GGCGAATGGCAGGAGCAG<u>ATG</u>ATGGGTTTTGACGTGGAGGATGTTC | 3 |
| TGTCTCAGCTGAGCCAAAATGAGAAGATTGCTCTCTTGTCCGGCATTGAT | |
| TTCTGGCATACTTATCCCATACCAAAGTACAACGTCCCTTCAGTCCGCCTA | |
| ACGGACGGTCCTAACGGCATACGAGGCACAAAGTTTTTTGCTGGCATTCC | |
| TGCTGCCTGCCTGCCATGTGGGACGGCCCTGGCCTCTACCTGGGATAAG | |
| CAGCTGCTGAAGAAGGCTGGGAAGCTGCTCGGTGATGAGTGCATCGCAA | |
| AAGGCGCCCACTGCTGGCTGGGCCCAACAATCAATACTCCCCGATCTCC | |

TABLE 1-continued

Sequences Provided In Support Of The Invention.

| Description | SEQ. ID NO. |
|---|---|

TCTGGGGGGCGCGGCTTCGAGTCATTTTCGGAAGATCCGTACCTGTCC

GGCATCCTTGCTGCATCTATGATTCTCGGCTGTGAAAGCACAGGTGTCAT

CTCTGCCGTCAAACACTTTGTCGCCAACGACCAGGAGCACGAGCGGCGA

GCGGTCGACTGTCTCATCACCCAGCGGGCTCTCCGGGAGGTCTATCTGC

GACCCTTCCAGATCGTAGCCCGAGATGCAAGGCCCGGCGCATTGATGAC

ATCCTACAACAAGGTCAATGGCAAGCACGTCGCTGACAGCGCCGAGTTC

CTTCAGGGCATTCTCCGGACTGAGTGGAATTGGGATCCTCTCATTGTCAG

CGACTGGTACGGCACCTACACCACTATTGATGCCATCAAAGCCGGCCTT

GATCTCGAGATGCCGGGCGTTTCACGATATCGCGGCAAATACATCGAGT

CTGCTCTGCAGGCCCGTTTGCTGAAGCAGTCCACTATCGATGAGCGCGC

TCGCCGCGTGCTCAGGTTCGCCCAGAAGGCCAGCCATCTCAAGGTCTCC

GAGGTAGAGCAAGGCCGTGACTTCCCAGAGGATCGCGTCCTCAACCGTC

AGATCTGCGGCAGCAGCATTGTCCTACTGAAGAATGAGAACTCCATCTTA

CCTCTCCCCAAGTCCGTCAAGAAGGTCGCCCTTGTTGGATCCCACGTGC

GTCTACCGGCTATCTCGGGAGGAGGCAGCGCCTCTCTTGTCCCTTACTAT

GCCATATCTCTATACGATGCCGTCTCTGAGGTACTAGCCGGTGCCACGAT

CACGCACGAGGTCGGTGCCTATGCCCACCAAATGCTGCCCGTCATCGAC

GCAATGATCAGCAACGCCGTAATCCACTTCTACAACGACCCCATCGATGT

CAAAGACAGAAAGCTCCTTGGCAGTGAGAACGTATCGTCGACATCGTTCC

AGCTCATGGATTACAACAACATCCCAACGCTCAACAAGGCCATGTTCTGG

GGTACTCTCGTGGGCGAGTTTATCCCTACCGCCACGGGAATTTGGGAATT

TGGCCTCAGTGTCTTTGGCACTGCCGACCTTTATATTGATAATGAGCTCG

TGATTGAAAATACAACACATCAGACGCGTGGTACCGCCTTTTTCGGAAAG

GGAACGACGGAAAAAGTCGCTACCAGGAGGATGGTGGCCGGCAGCACC

TACAAGCTGCGTCTCGAGTTTGGGTCTGCCAACACGACCAAGATGGAGA

CGACCGGTGTTGTCAACTTTGGCGGCGGTGCCGTACACCTGGGTGCCTG

TCTCAAGGTCGACCCCACAGGAGATGATTGCGCGGGCCGTCAAGGCCGCA

GCCGATGCCGACTACACCATCATCTGCACGGGACTCAGCGGCGAGTGG

GAGTCTGAGGGTTTTGACCGGCCTCACATGGACCTGCCCCCTGGTGTGG

ACACCATGATCTCGCAAGTTCTTGACGCCGCTCCCAATGCTGTAGTCGTC

AACCAGTCAGGCACCCCAGTGACAATGAGCTGGGCTCATAAAGCAAAGG

CCATTGTGCAGGCTTGGTATGGTGGTAACGAGACAGGCCACGGAATCTC

CGATGTGCTCTTTGGCAACGTCAACCCGTCGGGGAAACTCTCCCTATCGT

GGCCAGTCGATGTGAAGCACAACCCAGCATATCTCAACTACGCCAGCGT

TGGTGGACGGGTCTTGTATGGCGAGGATGTTTACGTTGGCTACAAGTTCT

ACGACAAAACGGAGAGGGAGGTTCTGTTTCCTTTTGGGCATGGCCTGTCT

TACGCTACCTTCAAGCTCCCAGATTCTACCGTGAGGACGGTCCCCGAAAC

TABLE 1-continued

Sequences Provided In Support Of The Invention.

| Description | SEQ. ID NO. |
|---|---|
| CTTCCACCCGGACCAGCCCACAGTAGCCATTGTCAAGATCAAGAACACG | |
| AGCAGTGTCCCGGGCGCCCAGGTCCTGCAGCTATACATTTCGGCCCCAA | |
| ACTCGCCTACACATCGCCCGGTCAAGGAGCTGCACGGATTCGAAAAGGT | |
| GTATCTTGAAGCTGGCGAGGAGAAGGAGGTACAAATACCCATTGACCAG | |
| TACGCTACTAGCTTCTGGGACGAGATTGAGAGCATGTGGAAGAGCGAGA | |
| GGGGCATTTATGATGTGCTTGTAGGATTCTCGAGTCAGGAAATCTCGGGC | |
| AAGGGGAAGCTGATTGTGCCTGAAACGCGATTCTGGATGGGGCTGTAG | |

The invention claimed is:

1. An enzymatic composition comprising: a BGL6 polypeptide having at least 90% sequence identity to the amino acid sequence as set forth in SEQ ID NO:2, an endoglucanase (EG), and a cellobiohydrolase (CBH), wherein the BGL6 polypeptide is from a different species than the EG and/or the CBH.

2. The enzymatic composition of claim 1, wherein the BGL6 polypeptide is from *Trichoderma reesei* and the EG is from a species other than *Trichoderma reesei*.

3. The enzymatic composition of claim 2, wherein the EG is selected from the group consisting of: EGI, EGII, EGIII, EGIV, and EGV endoglucanase.

4. The enzymatic composition of claim 3, wherein the EG is an EGIV endoglucanase.

5. The enzymatic composition of claim 1, wherein the BGL6 polypeptide is from *Trichoderma reesei* and the CBH is from a species other than *Trichoderma reesei*.

6. The enzymatic composition of claim 5, wherein the endoglucanase is selected from the group consisting of: CBHI and CBHII cellobiohydrolase.

7. The enzymatic composition of claim 1, wherein the enzymatic composition is a fermentation culture derived from a recombinant host cell.

8. The enzymatic composition of claim 7, wherein the recombinant host cell is a filamentous fungi or yeast cell.

9. The enzymatic composition of claim 8, wherein the recombinant host cell is a filamentous fungi selected from the group consisting of: *Trichoderma reesei, Trichoderma longibrachiatum, Trichoderma viride, Trichoderma koningii; Penicillium* sp., *Humicola* sp., *Aspergillus* sp., *Chrysosporium* sp., *Fusarium* sp., *Hypocrea* sp., and *Emericella* sp.

10. A method of producing ethanol comprising:
a) contacting a biomass composition with the enzymatic composition of claim 1 to yield a sugar solution;
b) adding to the sugar solution a fermentative microorganism; and
c) culturing the fermentative microorganism under conditions sufficient to produce ethanol.

11. The method of claim 10 further comprising pretreating the biomass composition prior to the contacting step (a).

12. The method of claim 11, wherein the pretreating comprises contacting the biomass composition with dilute acid.

13. A method of producing ethanol, said method comprising:
a) contacting a biomass composition with the enzymatic composition of claim 1 and a fermentative microorganism; and
b) culturing the fermentative microorganism under conditions sufficient to produce ethanol.

14. The method of claim 13 further comprising pretreating the biomass composition prior to the contacting step (a).

15. The method of claim 14, wherein the pretreating comprises contacting the biomass composition with dilute acid.

* * * * *

SEQUENCE LISTING

<160> NUMBER OF SEQ ID NOS: 4

<210> SEQ ID NO 1
<211> LENGTH: 2812
<212> TYPE: DNA
<213> ORGANISM: Trichoderma reesei

<400> SEQUENCE: 1

```
gatcacaccc ctcccaccct tctcttttca aggttgtccc cttctcccac ggctttatgt      60
acttcccact ctmtaattcg ctctttccat tccaagccaa gcaacatctg tgagcagctc     120
atccttccca atatgggcga atggcaggag cagatgatgg ttttgacgt ggaggatgtt      180
ctgtctcagc tgagccaaaa tgagaagatt gctctcttgt ccggcattga tttctggcat     240
acttatccca taccaaagta caacgtccct tcagtccgcc taacgacgg tcctaacggc      300
atacgaggca caaagttttt tgctggcatt cctgctgcct gcctgccatg tgggacggcc     360
ctggcctcta cctgggataa gcagctgctg aagaaggctg ggaagctgct cggtgatgag     420
tgcatcgcaa aaggcgccca ctgctggctg ggcccaacaa tcaatactcc ccgatctcct     480
ctgggggggc gcggcttcga gtcattttcg gaagatccgt acctgtccgg catccttgct     540
gcatctatga ttctcggctg tgaaagcaca ggtgtcatct ctgccgtcaa acactttgtc     600
gccaacgacc aggagcacga gcggcgagcg gtcgactgtc tcatcaccca gcgggctctc     660
cgggaggtct atctgcgacc cttccagatc gtagcccgag atgcaaggcc cggcgcattg     720
atgacatcct acaacaaggt caatggcaag cacgtcgctg acagcgccga gttccttcag     780
ggcattctcc ggactgagtg gaattgggat cctctcattg tcagcgactg gtacggcacc     840
tacaccacta ttgatgccat caaagccggc cttgatctcg agatgccggg cgtttcacga     900
tatcgcggca aatacatcga gtctgctctg caggcccgtt tgctgaagca gtccactatc     960
gatgagcgcg ctcgccgcgt gctcaggttc gcccagaagg ccagccatct caaggtctcc    1020
gaggtagagc aaggccgtga cttcccagag gatcgcgtcc tcaaccgtca gatctgcggc    1080
agcagcattg tcctactgaa gaatgagaac tccatcttac ctctccccaa gtccgtcaag    1140
aaggtcgccc ttgttggatc ccacgtgcgt ctaccggcta tctcgggagg aggcagcgcc    1200
tctcttgtcc cttactatgc catatctcta tacgatgccg tctctgaggt actagccggt    1260
gccacgatca cgcacgaggt cggtgcctat gcccaccaaa tgctgcccgt catcgacgca    1320
atgatcagca acgccgtaat ccacttctac aacgacccca tcgatgtcaa agacagaaag    1380
```

-continued

```
ctccttggca gtgagaacgt atcgtcgaca tcgttccagc tcatggatta caacaacatc    1440
ccaacgctca acaaggccat gttctggggt actctcgtgg gcgagtttat ccctaccgcc    1500
acgggaattt gggaatttgg cctcagtgtc tttggcactg ccgacccttta tattgataat   1560 gagctcgtga ttgaaaatac aacacatcag acgcgtggta ccgcctttttt cggaaaggga  1620 acgacggaaa aagtcgctac caggaggatg gtggccggca gcacctacaa gctgcgtctc    1680
gagtttgggt ctgccaacac gaccaagatg gagacgaccg tgttgtcaa ctttggcggc    1740 ggtgccgtac acctgggtgc ctgtctcaag gtcgacccac aggagatgat gcgcgggcc    1800 gtcaaggccg cagccgatgc cgactacacc atcatctgca cgggactcag cggcgagtgg    1860
gagtctgagg gttttgaccg gcctcacatg gacctgcccc ctggtgtgga caccatgatc   1920
tcgcaagttc ttgacgccgc tcccaatgct gtagtcgtca accagtcagg cacccagtg    1980 acaatgagct gggctcataa agcaaaggcc attgtgcagg cttggtatgg tggtaacgag   2040
acaggccacg gaatctccga tgtgctcttt ggcaacgtca cccgtcggg gaaactctcc    2100 ctatcgtggc cagtcgatgt gaagcacaac ccagcatatc tcaactacgc cagcgttggt   2160
ggacgggtct tgtatggcga ggatgtttac gttggctaca gttctacga caaaacggag    2220 agggaggttc tgtttccttt tgggcatggc ctgtcttacg ctaccttcaa gctcccagat    2280
tctaccgtga ggacggtccc cgaaaccttc caccccggacc agcccacagt agccattgtc   2340
aagatcaaga acacgagcag tgtcccgggc gcccaggtcc tgcagctata catttcggcc    2400
ccaaactcgc ctacacatcg cccggtcaag gagctgcacg gattcgaaaa ggtgtatctt    2460
gaagctggcg aggagaagga ggtacaaata cccattgacc agtacgctac tagcttctgg    2520
gacgagattg agagcatgtg gaagagcgag aggggcattt atgatgtgct tgtaggattc    2580
tcgagtcagg aaatctcggg caaggggaag ctgattgtgc ctgaaacgcg attctggatg    2640
gggctgtaga ttcaacacgt gagcaaaagc gattgcggaa agtaccagaa aagccaaggg    2700
agtcaaagga tgggaacttg tgtcaataga agatatgcat gatgggcatt tgggatggtg    2760
tttggcatta tgcaaagaag caaagatgga gtgataaaaa aaaaaaaaa aa            2812
```

<210> SEQ ID NO 2
<211> LENGTH: 838
<212> TYPE: PRT
<213> ORGANISM: Trichoderma reesei

<400> SEQUENCE: 2

```
Met Gly Glu Trp Gln Glu Gln Met Met Gly Phe Asp Val Glu Asp Val
 1               5                  10                  15

Leu Ser Gln Leu Ser Gln Asn Glu Lys Ile Ala Leu Ser Gly Ile
            20                  25                  30

Asp Phe Trp His Thr Tyr Pro Ile Pro Lys Tyr Asn Val Pro Ser Val
        35                  40                  45

Arg Leu Thr Asp Gly Pro Asn Gly Ile Arg Gly Thr Lys Phe Phe Ala
    50                  55                  60

Gly Ile Pro Ala Ala Cys Leu Pro Cys Gly Thr Ala Leu Ala Ser Thr
65                  70                  75                  80

Trp Asp Lys Gln Leu Leu Lys Lys Ala Gly Lys Leu Leu Gly Asp Glu
                85                  90                  95

Cys Ile Ala Lys Gly Ala His Cys Trp Leu Gly Pro Thr Ile Asn Thr
            100                 105                 110

Pro Arg Ser Pro Leu Gly Gly Arg Gly Phe Glu Ser Phe Ser Glu Asp
```

-continued

```
            115                 120                 125
Pro Tyr Leu Ser Gly Ile Leu Ala Ala Ser Met Ile Leu Gly Cys Glu
130                 135                 140
Ser Thr Gly Val Ile Ser Ala Val Lys His Phe Val Ala Asn Asp Gln
145                 150                 155                 160
Glu His Glu Arg Arg Ala Val Asp Cys Leu Ile Thr Gln Arg Ala Leu
                    165                 170                 175
Arg Glu Val Tyr Leu Arg Pro Phe Gln Ile Val Ala Arg Asp Ala Arg
            180                 185                 190
Pro Gly Ala Leu Met Thr Ser Tyr Asn Lys Val Asn Gly Lys His Val
            195                 200                 205
Ala Asp Ser Ala Glu Phe Leu Gln Gly Ile Leu Arg Thr Glu Trp Asn
210                 215                 220
Trp Asp Pro Leu Ile Val Ser Asp Trp Tyr Gly Thr Tyr Thr Thr Ile
225                 230                 235                 240
Asp Ala Ile Lys Ala Gly Leu Asp Leu Glu Met Pro Gly Val Ser Arg
                    245                 250                 255
Tyr Arg Gly Lys Tyr Ile Glu Ser Ala Leu Gln Ala Arg Leu Leu Lys
            260                 265                 270
Gln Ser Thr Ile Asp Glu Arg Ala Arg Arg Val Leu Arg Phe Ala Gln
            275                 280                 285
Lys Ala Ser His Leu Lys Val Ser Glu Val Gln Gly Arg Asp Phe
290                 295                 300
Pro Glu Asp Arg Val Leu Asn Arg Gln Ile Cys Gly Ser Ser Ile Val
305                 310                 315                 320
Leu Leu Lys Asn Glu Asn Ser Ile Leu Pro Leu Pro Lys Ser Val Lys
                    325                 330                 335
Lys Val Ala Leu Val Gly Ser His Val Arg Leu Pro Ala Ile Ser Gly
            340                 345                 350
Gly Gly Ser Ala Ser Leu Val Pro Tyr Tyr Ala Ile Ser Leu Tyr Asp
            355                 360                 365
Ala Val Ser Glu Val Leu Ala Gly Ala Thr Ile Thr His Glu Val Gly
370                 375                 380
Ala Tyr Ala His Gln Met Leu Pro Val Ile Asp Ala Met Ile Ser Asn
385                 390                 395                 400
Ala Val Ile His Phe Tyr Asn Asp Pro Ile Asp Val Lys Asp Arg Lys
                    405                 410                 415
Leu Leu Gly Ser Glu Asn Val Ser Ser Thr Ser Phe Gln Leu Met Asp
            420                 425                 430
Tyr Asn Asn Ile Pro Thr Leu Asn Lys Ala Met Phe Trp Gly Thr Leu
            435                 440                 445
Val Gly Glu Phe Ile Pro Thr Ala Thr Gly Ile Trp Glu Phe Gly Leu
450                 455                 460
Ser Val Phe Gly Thr Ala Asp Leu Tyr Ile Asp Asn Glu Leu Val Ile
465                 470                 475                 480
Glu Asn Thr Thr His Gln Thr Arg Gly Thr Ala Phe Phe Gly Lys Gly
                    485                 490                 495
Thr Thr Glu Lys Val Ala Thr Arg Met Val Ala Gly Ser Thr Tyr
            500                 505                 510
Lys Leu Arg Leu Glu Phe Gly Ser Ala Asn Thr Thr Lys Met Glu Thr
            515                 520                 525
Thr Gly Val Val Asn Phe Gly Gly Gly Ala Val His Leu Gly Ala Cys
530                 535                 540
```

Leu Lys Val Asp Pro Gln Glu Met Ile Ala Arg Ala Val Lys Ala Ala
545                 550                 555                 560

Ala Asp Ala Asp Tyr Thr Ile Ile Cys Thr Gly Leu Ser Gly Glu Trp
            565                 570                 575

Glu Ser Glu Gly Phe Asp Arg Pro His Met Asp Leu Pro Pro Gly Val
        580                 585                 590

Asp Thr Met Ile Ser Gln Val Leu Asp Ala Ala Pro Asn Ala Val Val
    595                 600                 605

Val Asn Gln Ser Gly Thr Pro Val Thr Met Ser Trp Ala His Lys Ala
610                 615                 620

Lys Ala Ile Val Gln Ala Trp Tyr Gly Asn Glu Thr Gly His Gly
625                 630                 635                 640

Ile Ser Asp Val Leu Phe Gly Asn Val Asn Pro Ser Gly Lys Leu Ser
            645                 650                 655

Leu Ser Trp Pro Val Asp Val Lys His Asn Pro Ala Tyr Leu Asn Tyr
        660                 665                 670

Ala Ser Val Gly Gly Arg Val Leu Tyr Gly Glu Asp Val Tyr Val Gly
    675                 680                 685

Tyr Lys Phe Tyr Asp Lys Thr Glu Arg Glu Val Leu Phe Pro Phe Gly
690                 695                 700

His Gly Leu Ser Tyr Ala Thr Phe Lys Leu Pro Asp Ser Thr Val Arg
705                 710                 715                 720

Thr Val Pro Glu Thr Phe His Pro Asp Gln Pro Thr Val Ala Ile Val
            725                 730                 735

Lys Ile Lys Asn Thr Ser Ser Val Pro Gly Ala Gln Val Leu Gln Leu
        740                 745                 750

Tyr Ile Ser Ala Pro Asn Ser Pro Thr His Arg Pro Val Lys Glu Leu
    755                 760                 765

His Gly Phe Glu Lys Val Tyr Leu Glu Ala Gly Glu Glu Lys Glu Val
770                 775                 780

Gln Ile Pro Ile Asp Gln Tyr Ala Thr Ser Phe Trp Asp Glu Ile Glu
785                 790                 795                 800

Ser Met Trp Lys Ser Glu Arg Gly Ile Tyr Asp Val Leu Val Gly Phe
            805                 810                 815

Ser Ser Gln Glu Ile Ser Gly Lys Gly Lys Leu Ile Val Pro Glu Thr
        820                 825                 830

Arg Phe Trp Met Gly Leu
        835

<210> SEQ ID NO 3
<211> LENGTH: 2517
<212> TYPE: DNA
<213> ORGANISM: Trichoderma reesei

<400> SEQUENCE: 3
atgggcgaat ggcaggagca gatgatgggt tttgacgtgg aggatgttct gtctcagctg     60
agccaaaatg agaagattgc tctcttgtcc ggcattgatt ctggcatac ttatcccata    120 ccaaagtaca acgtcccttc agtccgccta acggacggtc ctaacggcat acgaggcaca    180
aagttttttg ctggcattcc tgctgcctgc ctgccatgtg ggacggccct ggcctctacc    240
tgggataagc agctgctgaa gaaggctggg aagctgctcg gtgatgagtg catcgcaaaa    300
ggcgcccact gctggctggg cccaacaatc aatactcccc gatcctcct gggggggcgc    360 ggcttcgagt cattttcgga agatccgtac ctgtccggca tccttgctgc atctatgatt    420

```
ctcggctgtg aaagcacagg tgtcatctct gccgtcaaac actttgtcgc caacgaccag    480
gagcacgagc ggcgagcggt cgactgtctc atcacccagc gggctctccg ggaggtctat    540
ctgcgaccct tccagatcgt agcccgagat gcaaggcccg gcgcattgat gacatcctac    600
aacaaggtca atggcaagca cgtcgctgac agcgccgagt ccttcaggg cattctccgg     660 actgagtgga attgggatcc tctcattgtc agcgactggt acggcaccta caccactatt    720
gatgccatca aagccggcct tgatctcgag atgccgggcg tttcacgata tcgcggcaaa    780
tacatcgagt ctgctctgca ggcccgtttg ctgaagcagt ccactatcga tgagcgcgct    840
cgccgcgtgc tcaggttcgc ccagaaggcc agccatctca aggtctccga ggtagagcaa    900
ggccgtgact tcccagagga tcgcgtcctc aaccgtcaga tctgcggcag cagcattgtc    960
ctactgaaga atgagaactc catcttacct ctccccaagt ccgtcaagaa ggtcgccctt   1020
gttggatccc acgtgcgtct accggctatc tcggaggag cagcgcctc tcttgtccct    1080 tactatgcca tatctctata cgatgccgtc tctgaggtac tagccggtgc cacgatcacg   1140
cacgaggtcg gtgcctatgc ccaccaaatg ctgcccgtca tcgacgcaat gatcagcaac   1200
gccgtaatcc acttctacaa cgaccccatc gatgtcaaag acagaaagct ccttggcagt   1260
gagaacgtat cgtcgacatc gttccagctc atggattaca caacatccc aacgctcaac    1320 aaggccatgt tctggggtac tctcgtgggc gagtttatcc ctaccgccac gggaatttgg   1380
gaatttggcc tcagtgtctt tggcactgcc gactttata ttgataatga gctcgtgatt     1440
gaaaatacaa cacatcagac gcgtggtacc gccttttttcg gaaagggaac gacggaaaaa   1500
gtcgctacca ggaggatggt ggccggcagc acctacaagc tgcgtctcga gtttgggtct   1560
gccaacacga ccaagatgga gacgaccggt gttgtcaact tggcggcgg tgccgtacac     1620 ctgggtgcct gtctcaaggt cgacccacag gagatgattg cgcgggccgt caaggccgca   1680
gccgatgccg actacaccat catctgcacg ggactcagcg gcgagtggga gtctgagggt   1740
tttgaccggc ctcacatgga cctgccccct ggtgtggaca ccatgatctc gcaagttctt   1800
gacgccgctc ccaatgctgt agtcgtcaac cagtcaggca ccccagtgac aatgagctgg   1860
gctcataaag caaaggccat tgtgcaggct tggtatggtg gtaacgagac aggccacgga   1920
atctccgatg tgctctttgg caacgtcaac ccgtcgggga aactctccct atcgtggcca   1980
gtcgatgtga agcacaaccc agcatatctc aactacgcca gcgttggtgg acgggtcttg   2040
tatggcgagg atgtttacgt tggctacaag ttctacgaca aaacggagag ggaggttctg   2100
tttccttttg gcatggcct gtcttacgct accttcaagc tcccagattc taccgtgagg    2160
acggtccccg aaaccttcca cccggaccag cccacagtag ccattgtcaa gatcaagaac   2220
acgagcagtg tcccgggcgc ccaggtcctg cagctataca tttcggcccc aaactcgcct   2280
acacatcgcc cggtcaagga gctgcacgga ttcgaaaagg tgtatcttga agctggcgag   2340
gagaaggagg tacaaatacc cattgaccag tacgctacta gcttctggga cgagattgag   2400
agcatgtgga agagcgagag gggcattat gatgtgcttg taggattctc gagtcaggaa    2460
atctcgggca aggggaagct gattgtgcct gaaacgcgat tctggatggg gctgtag      2517
```

<210> SEQ ID NO 4
<211> LENGTH: 831
<212> TYPE: PRT
<213> ORGANISM: Trichoderma reesei

<400> SEQUENCE: 4

```
Met Met Gly Phe Asp Val Glu Asp Val Leu Ser Gln Leu Ser Gln Asn
 1               5                  10                  15
Glu Lys Ile Ala Leu Leu Ser Gly Ile Asp Phe Trp His Thr Tyr Pro
            20                  25                  30
Ile Pro Lys Tyr Asn Val Pro Ser Val Arg Leu Thr Asp Gly Pro Asn
        35                  40                  45
Gly Ile Arg Gly Thr Lys Phe Phe Ala Gly Ile Pro Ala Ala Cys Leu
 50                  55                  60
Pro Cys Gly Thr Ala Leu Ala Ser Thr Trp Asp Lys Gln Leu Leu Lys
 65                  70                  75                  80
Lys Ala Gly Lys Leu Leu Gly Asp Glu Cys Ile Ala Lys Gly Ala His
                85                  90                  95
Cys Trp Leu Gly Pro Thr Ile Asn Thr Pro Arg Ser Pro Leu Gly Gly
            100                 105                 110
Arg Gly Phe Glu Ser Phe Ser Glu Asp Pro Tyr Leu Ser Gly Ile Leu
        115                 120                 125
Ala Ala Ser Met Ile Leu Gly Cys Glu Ser Thr Gly Val Ile Ser Ala
130                 135                 140
Val Lys His Phe Val Ala Asn Asp Gln Glu His Glu Arg Arg Ala Val
145                 150                 155                 160
Asp Cys Leu Ile Thr Gln Arg Ala Leu Arg Glu Val Tyr Leu Arg Pro
                165                 170                 175
Phe Gln Ile Val Ala Arg Asp Ala Arg Pro Gly Ala Leu Met Thr Ser
            180                 185                 190
Tyr Asn Lys Val Asn Gly Lys His Val Ala Asp Ser Ala Glu Phe Leu
        195                 200                 205
Gln Gly Ile Leu Arg Thr Glu Trp Asn Trp Asp Pro Leu Ile Val Ser
210                 215                 220
Asp Trp Tyr Gly Thr Tyr Thr Thr Ile Asp Ala Ile Lys Ala Gly Leu
225                 230                 235                 240
Asp Leu Glu Met Pro Gly Val Ser Arg Tyr Arg Gly Lys Tyr Ile Glu
                245                 250                 255
Ser Ala Leu Gln Ala Arg Leu Leu Lys Gln Ser Thr Ile Asp Glu Arg
            260                 265                 270
Ala Arg Arg Val Leu Arg Phe Ala Gln Lys Ala Ser His Leu Lys Val
        275                 280                 285
Ser Glu Val Glu Gln Gly Arg Asp Phe Pro Glu Asp Arg Val Leu Asn
290                 295                 300
Arg Gln Ile Cys Gly Ser Ser Ile Val Leu Leu Lys Asn Glu Asn Ser
305                 310                 315                 320
Ile Leu Pro Leu Pro Lys Ser Val Lys Lys Val Ala Leu Val Gly Ser
                325                 330                 335
His Val Arg Leu Pro Ala Ile Ser Gly Gly Ser Ala Ser Leu Val
            340                 345                 350
Pro Tyr Tyr Ala Ile Ser Leu Tyr Asp Ala Val Ser Glu Val Leu Ala
        355                 360                 365
Gly Ala Thr Ile Thr His Glu Val Gly Ala Tyr Ala His Gln Met Leu
370                 375                 380
Pro Val Ile Asp Ala Met Ile Ser Asn Ala Val Ile His Phe Tyr Asn
385                 390                 395                 400
Asp Pro Ile Asp Val Lys Asp Arg Lys Leu Leu Gly Ser Glu Asn Val
                405                 410                 415
Ser Ser Thr Ser Phe Gln Leu Met Asp Tyr Asn Asn Ile Pro Thr Leu
```

-continued

```
                420                 425                 430
Asn Lys Ala Met Phe Trp Gly Thr Leu Val Gly Glu Phe Ile Pro Thr
            435                 440                 445

Ala Thr Gly Ile Trp Glu Phe Gly Leu Ser Val Phe Gly Thr Ala Asp
        450                 455                 460

Leu Tyr Ile Asp Asn Glu Leu Val Ile Glu Asn Thr Thr His Gln Thr
465                 470                 475                 480

Arg Gly Thr Ala Phe Phe Gly Lys Gly Thr Thr Glu Lys Val Ala Thr
                485                 490                 495

Arg Arg Met Val Ala Gly Ser Thr Tyr Lys Leu Arg Leu Glu Phe Gly
            500                 505                 510

Ser Ala Asn Thr Thr Lys Met Glu Thr Thr Gly Val Val Asn Phe Gly
        515                 520                 525

Gly Gly Ala Val His Leu Gly Ala Cys Leu Lys Val Asp Pro Gln Glu
    530                 535                 540

Met Ile Ala Arg Ala Val Lys Ala Ala Ala Asp Ala Asp Tyr Thr Ile
545                 550                 555                 560

Ile Cys Thr Gly Leu Ser Gly Glu Trp Glu Ser Glu Gly Phe Asp Arg
                565                 570                 575

Pro His Met Asp Leu Pro Pro Gly Val Asp Thr Met Ile Ser Gln Val
            580                 585                 590

Leu Asp Ala Ala Pro Asn Ala Val Val Asn Gln Ser Gly Thr Pro
        595                 600                 605

Val Thr Met Ser Trp Ala His Lys Ala Lys Ala Ile Val Gln Ala Trp
    610                 615                 620

Tyr Gly Gly Asn Glu Thr Gly His Gly Ile Ser Asp Val Leu Phe Gly
625                 630                 635                 640

Asn Val Asn Pro Ser Gly Lys Leu Ser Leu Ser Trp Pro Val Asp Val
                645                 650                 655

Lys His Asn Pro Ala Tyr Leu Asn Tyr Ala Ser Val Gly Gly Arg Val
            660                 665                 670

Leu Tyr Gly Glu Asp Val Tyr Val Gly Tyr Lys Phe Tyr Asp Lys Thr
        675                 680                 685

Glu Arg Glu Val Leu Phe Pro Phe Gly His Gly Leu Ser Tyr Ala Thr
    690                 695                 700

Phe Lys Leu Pro Asp Ser Thr Val Arg Thr Val Pro Glu Thr Phe His
705                 710                 715                 720

Pro Asp Gln Pro Thr Val Ala Ile Val Lys Ile Lys Asn Thr Ser Ser
                725                 730                 735

Val Pro Gly Ala Gln Val Leu Gln Leu Tyr Ile Ser Ala Pro Asn Ser
            740                 745                 750

Pro Thr His Arg Pro Val Lys Glu Leu His Gly Phe Glu Lys Val Tyr
        755                 760                 765

Leu Glu Ala Gly Glu Glu Lys Glu Val Gln Ile Pro Ile Asp Gln Tyr
    770                 775                 780

Ala Thr Ser Phe Trp Asp Glu Ile Glu Ser Met Trp Lys Ser Glu Arg
785                 790                 795                 800

Gly Ile Tyr Asp Val Leu Val Gly Phe Ser Ser Gln Glu Ile Ser Gly
                805                 810                 815

Lys Gly Lys Leu Ile Val Pro Glu Thr Arg Phe Trp Met Gly Leu
            820                 825                 830
```